US010189878B2

(12) United States Patent
Clinton et al.

(10) Patent No.: US 10,189,878 B2
(45) Date of Patent: Jan. 29, 2019

(54) EBOLAVIRUS PRE-HAIRPIN INTERMEDIATE MIMICS AND METHODS OF USE

(71) Applicants: UNIVERSITY OF UTAH RESEARCH FOUNDATION, Salt Lake City, UT (US); Tracy R. Clinton, Charlottesville, VA (US)

(72) Inventors: Tracy R. Clinton, Charlottesville, VA (US); Michael Thomas Jacobsen, Salt Lake City, UT (US); Matthew T. Weinstock, San Diego, CA (US); Brett D. Welch, Salt Lake City, UT (US); Debra Muir Eckert, Salt Lake City, UT (US); Michael S. Kay, Salt Lake City, UT (US)

(73) Assignees: University of Utah Research Foundation, Salt Lake City, UT (US); Navigen, Inc., Salt Lake City, UT (US); The United States of America—Air Force, Washington, DC (US)

( * ) Notice: Subject to any disclaimer, the term of this patent is extended or adjusted under 35 U.S.C. 154(b) by 0 days.

(21) Appl. No.: 15/513,959

(22) PCT Filed: Sep. 24, 2015

(86) PCT No.: PCT/US2015/052061
§ 371 (c)(1),
(2) Date: Mar. 23, 2017

(87) PCT Pub. No.: WO2016/049380
PCT Pub. Date: Mar. 31, 2016

(65) Prior Publication Data
US 2017/0247418 A1 Aug. 31, 2017

Related U.S. Application Data

(60) Provisional application No. 62/054,835, filed on Sep. 24, 2014.

(51) Int. Cl.
*A61K 38/00* (2006.01)
*C07K 14/005* (2006.01)
*C07K 14/08* (2006.01)
*G01N 33/68* (2006.01)

(52) U.S. Cl.
CPC ............ *C07K 14/005* (2013.01); *C07K 14/08* (2013.01); *G01N 33/6845* (2013.01); *A61K 38/00* (2013.01); *C12N 2760/14122* (2013.01); *C12N 2760/14133* (2013.01); *G01N 2333/08* (2013.01); *G01N 2500/04* (2013.01)

(58) Field of Classification Search
None
See application file for complete search history.

(56) References Cited

U.S. PATENT DOCUMENTS

| 3,610,795 | A | 10/1971 | Jacques et al. |
| 6,713,069 | B1 | 3/2004 | Gallaher |
| 2004/0044183 | A1 | 3/2004 | Eckert et al. |
| 2006/0280754 | A1 | 12/2006 | Garry |
| 2007/0185025 | A1 | 8/2007 | Palacios et al. |
| 2013/0259887 | A1 | 10/2013 | Dermody et al. |
| 2014/0323392 | A1 | 10/2014 | Francis et al. |

FOREIGN PATENT DOCUMENTS

EP    0 045 665 A1    2/1982

OTHER PUBLICATIONS

Adams et al., "*PHENIX*: a comprehensive Python-based system for macromolecular structure solution," *Acta Crystallographica Section D: Biological Crystallography* 66(Part 2):213-221, 2010.
Anthony-Cahill et al., "Site-specific mutagenesis with unnatural amino acids," *Trends in Biochemical Sciences* 14(10):400-403, 1989.
Baize et al., "Emergence of Zaire Ebola Virus Disease in Guinea," t*The New England Journal of Medicine*371(15):1418-1425, 2014.
Basu et al., "Identification of a Small-Molecule Entry Inhibitor for Filoviruses," *Journal of Virology* 85(7):3106-3119, 2011.
Benner, "Expanding the genetic lexicon: incorporating nonstandard amino acids into proteins by ribosome-based synthesis," *Trends in Biotechnology* 12(2):158-162, 1994.
Blanco-Canosa et al., "An efficient Fmoc-SPPS approach for the generation of thioester peptide precursors for use in native chemical ligation," *Angewandte Chemie International Edition* 47(36):6851-6855, 2008. (10 pages).
Carette et al., "Ebola virus entry requires the cholesterol transporter Niemann-Pick C1," *Nature* 477(7364):340-343, 2011. (21 pages).
Centers for Disease Control and Prevention, "Outbreaks Chronology: Ebola Virus Disease," Dec. 30, 2014, URL=http://www.web.archive.org/web/20141229091912/http://www.cdc.gov/vhf/ebola/outbreaks/history/chronology.html, download date Jul. 21, 2017, 7 pages.
Chan et al., "Core Structure of gp41 from the HIV Envelope Glycoprotein," *Cell* 89(2):263-273, 1997.
Chandran et al., "Endosomal Proteolysis of the Ebola Virus Glycoprotein Is Necessary for Infection," *Science* 308(5728):1643-1645, 2005. (8 pages).
Chen et al., "Distinct Modes of Human Immunodeficiency Virus Type 1 Proviral Latency Revealed by Superinfection of Nonproductively Infected Cell Lines with Recombinant Luciferase-Encoding Viruses," *Journal of Virology* 68(2):654-660, 1994.
Chen et al., "*MolProbity*: all-atom structure validation for macromolecular crystallography," *Acta Crystallographica Section D: Biological Crystallography* 66(Part 1):12-21, 2010.
Clinton et al., "Design and characterization of ebolavirus GP prehairpin intermediate mimics as drug targets," *Protein Science* 24(4):446-463, 2015.
Cole, "Analysis of Heterogeneous Interactions," *Methods in Enzymology* 384:212-232, 2004. (19 pages).

(Continued)

Primary Examiner — Thomas S Heard
(74) Attorney, Agent, or Firm — Seed IP Law Group LLP

(57) ABSTRACT

Ebolavirus is a highly lethal filovirus that causes hemorrhagic fever in humans and non-human primates. With no approved treatments or preventatives, the development of an anti-*ebolavirus* therapy to protect against natural infections and potential weaponization is an urgent unmet global health need. The design, biophysical characterization, and validation of peptide mimics of the *ebolavirus* N-trimer ("N-trimer mimics") are described herein.

6 Claims, 18 Drawing Sheets
Specification includes a Sequence Listing.

(56) References Cited

OTHER PUBLICATIONS

Connor et al., "Vpr Is Required for Efficient Replication of Human Immunodeficiency Virus Type-1 in Mononuclear Phagocytes," *Virology* 206(2):935-944, 1995.

Côté et al., "Small molecule inhibitors reveal Niemann-Pick C1 is essential for ebolavirus infection," *Nature* 477(7364):344-348, 2011. (15 pages).

Deng et al., "Identification of a major co-receptor for primary isolates of HIV-1," *Nature* 381(6584):661-666, 1996.

Dintzis et al., "A Comparison of the Immunogenicity of a Pair of Enantiomeric Proteins," *Proteins: Structure, Function, and Genetics* 16(3):306-308, 1993.

Dye et al., "Postexposure antibody prophylaxis protects nonhuman primates from filovirus disease," *Proceedings of the National Academy of Sciences of the United States of America* 109(13):5034-5039, 2012.

Eckert et al., "Design of potent inhibitors of HIV-1 entry from the gp41 N-peptide region," *Proceedings of the National Academy of Sciences of the United States of America* 98(20):11187-11192, 2001.

Eckert et al., "Inhibiting HIV-1 Entry: Discovery of D-Peptide Inhibitors that Target the gp41 Coiled-Coil Pocket," *Cell* 99(1):103-115, 1999.

Eckert et al., "Mechanisms of Viral Membrane Fusion and Its Inhibition," *Annual Review of Biochemistry* 70:777-810, 2001. (36 pages).

Eckert et al., "Crystal Structure of GCN4-pI$_Q$I, a Trimeric Coiled Coil with Buried Polar Residues," *Journal of Molecular Biology* 284(4):859-865, 1998.

Edelhoch, "Spectroscopic Determination of Tryptophan and Tyrosine in Proteins," *Biochemistry* 6(7):1948-1954, 1967.

Emsley et al., "Coot: model-building tools for molecular graphics," *Acta Crystallographica* D60(12):2126-2132, 2004.

Francis et al., "Design of a modular tetrameric scaffold for the synthesis of membrane-localized D-peptide inhibitors of HIV-1 entry," *Bioconjugate Chemistry* 23(6):1252-1258, 2012. (15 pages).

Geisbert et al., "Postexposure protection of non-human primates against a lethal Ebola virus challenge with RNA interference: a proof-of-concept study," *The Lancet* 375(9729):1896-1905, 2010.

Hackenberger et al., "Chemoselective Ligation and Modification Strategies for Peptides and Proteins," *Angewandte Chemie International Edition* 47(52):10030-10074, 2008.

Hamburger et al., "Steric Accessibility of the HIV-1 gp41 N-trimer Region," *The Journal of Biological Chemistry* 280(13):12567-12572, 2005. (7 pages).

Harrison et al., "Designed protein mimics of the Ebola virus glycoprotein GP2 α-helical bundle: Stability and pH effects," *Protein Science* 20(9):1587-1596, 2011.

He et al., "Human Immunodeficiency Virus Type 1 Viral Protein R (Vpr) Arrests Cells in the $G_2$ Phase of the Cell Cycle by Inhibiting p34$^{cdc2}$ Activity," *Journal of Virology* 69(11):6705-6711, 1995.

Henikoff et al., "Amino acid substitution matrices from protein blocks," *Proceedings of the National Academy of Sciences of the United States of America* 89(22):10915-10919, 1992.

Higgins et al., "C-peptide inhibitors of Ebola virus glycoprotein-mediated cell entry: Effects of conjugation to cholesterol and side chain-side chain crosslinking," *Bioorganic & Medicinal Chemistry Letters* 23(19):5356-5360, 2013. (11 pages).

Ibba et al., "Towards Engineering Proteins by Site-Directed Incorporation In Vivo of Non-Natural Amino Acids," *Bio/technology* 12(7):678-682, 1994.

Ibba, "Strategies for in vitro and in vivo translation with non-natural amino acids," *Biotechnology and Genetic Engineering Reviews* 13:197-216, 1995.

International Search Report and Written Opinion, dated Dec. 29, 2015, for International Application No. PCT/US2015/052061, 12 pages.

Jeffers et al., "Covalent Modifications of the Ebola Virus Glycoprotein," *Journal of Virology* 76(24):12463-12472, 2002.

Joshi et al., "A Core Trimer of the Paramyxovirus Fusion Protein: Parallels to Influenza Virus Hemagglutinin and HIV-1 gp41," *Virology* 248(1):20-34, 1998.

Kuhn et al., "Conserved Receptor-binding Domains of Lake Victoria Marburgvirus and Zaire Ebolavirus Bind a Common Receptor," *The Journal of Biological Chemistry* 281(23):15951-15958, 2006.

Landau et al., "Packaging System for Rapid Production of Murine Leukemia Virus Vectors with Variable Tropism," *Journal of Virology* 66(8):5110-5113, 1992.

Lee et al., "*Ebolavirus* glycoprotein structure and mechanism of entry," *Future Virology* 4(6):621-635, 2009. (23 pages).

Liu et al., "Identification of a minimal peptide derived from heptad repeat (HR) 2 of spike protein of SARS-CoV and combination of HR1-derived peptides as fusion inhibitors," *Antiviral Research* 81(1):82-87, 2009.

Malashkevich et al., "Core structure of the envelope glycoprotein GP2 from Ebola virus at 1.9-Å resolution," *Proceedings of the National Academy of Sciences of the United States of America* 96(6):2662-2667, 1999.

Marzi et al., "Vesicular Stomatitis Virus-Based Vaccines for Prophylaxis and Treatment of Filovirus Infections," *Journal of Bioterrorism & Biodefense* S1(4):004, 2011. (16 pages).

McCoy et al., "Phaser crystallographic software," *Journal of Applied Crystallography* 40(Part 4):658-674, 2007.

Miller et al., "A human monoclonal antibody neutralizes diverse HIV-1 isolates by binding a critical gp41 epitope," *Proceedings of the National Academy of Sciences of the United States of America* 102(41):14759-14764, 2005.

Miller et al., "Inhibition of Ebola Virus Entry by a C-peptide Targeted to Endosomes," *The Journal of Biological Chemistry* 286(18):15854-15861, 2011.

Misasi et al., "Filoviruses Require Endosomal Cysteine Proteases for Entry but Exhibit Distinct Protease Preferences," *Journal of Virology* 86(6):3284-3292, 2012.

Montgomery et al., "Affinity maturation and characterization of a human monoclonal antibody against HIV-1 gp41," *mAbs* 1(5):462-474, 2009.

Noren et al., "Construction of High-Complexity Combinatorial Phage Display Peptide Libraries," *Methods* 23(2):169-178, 2001.

O'Shannessy et al., "Determination of Rate and Equilibrium Binding Constants for Macromolecular Interactions Using Surface Plasmon Resonance: Use of Nonlinear Least Squares Analysis Methods," *Analytical Biochemistry* 212(2):457-468, 1993.

Otwinowski et al., "Processing of X-Ray Diffraction Data Collected in Oscillation Mode," *Methods in Enzymology* 276:307-326, 1997.

Qiu et al., "Successful Treatment of Ebola Virus-Infected Cynomolgus Macaques with Monoclonal Antibodies," *Science Translational Medicine* 4(138):138ra81, 2012. (12 pages).

Rizo et al., "Constrained Peptides: Models of Bioactive Peptides and Protein Substructures," *Annual Review of Biochemistry* 61:387-418, 1992.

Roffey et al., "Biological warfare in a historical perspective," *Clinical Microbiology and Infection* 8(8):450-454, 2002.

Root et al., "HIV-1 gp41 as a Target for Viral Entry Inhibition," *Current Pharmaceutical Design* 10(15):1805-1825, 2004. (22 pages).

Salerno et al., "MONSTER: inferring non-covalent interactions in macromolecular structures from atomic coordinate data," *Nucleic Acids Research* 32(Web Server):W566-W568, 2004.

Sanchez et al., "The virion glycoproteins of Ebola viruses are encoded in two reading frames and are expressed through transcriptional editing," *Proceedings of the National Academy of Sciences of the United States of America* 93(8):3602-3607, 1996.

Schornberg et al., "Role of Endosomal Cathepsins in Entry Mediated by the Ebola Virus Glycoprotein," *Journal of Virology* 80(8):4174-4178, 2006.

Schumacher et al., "Identification of D-Peptide Ligands Through Mirror-Image Phage Display," *Science* 271(5257):1854-1857, 1996.

Studier, "Protein production by auto-induction in high-density shaking cultures," *Protein Expression & Purification* 41(1):207-234, 2005.

(56) References Cited

OTHER PUBLICATIONS

Thorson et al., "A Biosynthetic Approach for the Incorporation of Unnatural Amino Acids into Proteins," *Methods in Molecular Biology* 77:43-73, 1998.

Volchkov et al., "Processing of the Ebola virus glycoprotein by the proprotein convertase furin," *Proceedings of the National Academy of Sciences of the United States of America* 95(10):5762-5767, 1998.

Volchkov et al., "Proteolytic Processing of Marburg Virus Glycoprotein," *Virology* 268(1):1-6, 2000.

Warren et al., "Advanced antisense therapies for postexposure protection against lethal filovirus infections," *Nature Medicine* 16(9):991-994, 2010.

Watanabe et al., "Functional Importance of the Coiled-Coil of the Ebola Virus Glycoprotein," *Journal of Virology* 74(21):10194-10201, 2000.

Weinstock et al., "Protease-Resistant Peptide Design—Empowering Nature's Fragile Warriors Against HIV," *Biopolymers* 98(5):431-442, 2012. (19 pages).

Weissenhorn et al., "Atomic structure of the ectodomain from HIV-1 gp41," *Nature* 387(6631):426-430, 1997.

Weissenhorn et al., "Crystal Structure of the Ebola Virus Membrane Fusion Subunit, GP2, from the Envelope Glycoprotein Ectodomain," *Molecular Cell* 2(5):605-616, 1998.

Welch et al., "Design of a Potent d-Peptide HIV-1 Entry Inhibitor with a Strong Barrier to Resistance," *Journal of Virology* 84(21):11235-11244, 2010. (11 pages).

Welch et al., "Potent D-peptide inhibitors of HIV-1 entry," *Proceedings of the National Academy of Sciences of the United States of America* 104(43):16828-16833, 2007.

White et al., "A new player in the puzzle of filovirus entry," *Nature Reviews Microbiology* 10(5):317-322, 2012. (14 pages).

Wild et al., "A Synthetic Peptide from HIV-1 gp41 Is a Potent Inhibitor of Virus-Mediated Cell-Cell Fusion," *AIDS Research and Human Retroviruses* 9(11):1051-1053, 1993.

Zawadzke et al., "A Racemic Protein," *Journal of the American Chemical Society* 114(10):4002-4003, 1992.

Zoller, "New recombinant DNA methodology for protein engineering," *Current Opinion in Biotechnology* 3(4):348-354, 1992.

SEQUENCE LISTING

```
<160> NUMBER OF SEQ ID NOS: 32

<210> SEQ ID NO 1
<211> LENGTH: 8
<212> TYPE: PRT
<213> ORGANISM: Artificial Sequence
<220> FEATURE:
<223> OTHER INFORMATION: 8 C-peptide residues for Ebola virus

<400> SEQUENCE: 1

Ile Thr Asp Lys Ile Asp Gln Ile
1               5

<210> SEQ ID NO 2
<211> LENGTH: 8
<212> TYPE: PRT
<213> ORGANISM: Artificial Sequence
<220> FEATURE:
<223> OTHER INFORMATION: 8 C-peptide residues for HIV
```

```
<400> SEQUENCE: 2

Trp Met Glu Trp Asp Arg Glu Ile
1               5

<210> SEQ ID NO 3
<211> LENGTH: 7
<212> TYPE: PRT
<213> ORGANISM: Artificial Sequence
<220> FEATURE:
<223> OTHER INFORMATION: TEV cleavage site

<400> SEQUENCE: 3

Glu Asn Leu Tyr Phe Gln Gly
1               5

<210> SEQ ID NO 4
<211> LENGTH: 101
<212> TYPE: PRT
<213> ORGANISM: Artificial Sequence
<220> FEATURE:
<223> OTHER INFORMATION: Recombinant peptide sequence
<220> FEATURE:
<221> NAME/KEY: VARIANT
<222> LOCATION: (1)...(101)
<223> OTHER INFORMATION: Xaa = Ala or Asp

<400> SEQUENCE: 4

Gly His Met Asp Ile Lys Lys Glu Ile Glu Ala Ile Lys Lys Glu Gln
1               5                   10                  15

Glu Ala Ile Lys Lys Lys Ile Glu Ala Ile Glu Lys Glu Leu Arg Gln
                20                  25                  30

Leu Ala Asn Glu Thr Thr Gln Xaa Leu Gln Leu Phe Leu Arg Xaa Thr
            35                  40                  45

Thr Glu Leu Arg Thr Phe Ser Ile Leu Asn Arg Lys Xaa Ile Asp Phe
        50                  55                  60

Leu Leu Gln Arg Met Lys Gln Ile Glu Asp Lys Ile Glu Glu Ile Glu
65                  70                  75                  80

Ser Lys Gln Lys Lys Ile Glu Asn Glu Ile Ala Arg Ile Lys Lys Leu
                85                  90                  95

Ile Gly Glu Arg Tyr
            100

<210> SEQ ID NO 5
<211> LENGTH: 10
<212> TYPE: PRT
<213> ORGANISM: Artificial Sequence
<220> FEATURE:
<223> OTHER INFORMATION: Recombinant peptide sequence

<400> SEQUENCE: 5

Gly His Met Cys Gly Gly Asp Ile Lys Lys
1               5                   10

<210> SEQ ID NO 6
<211> LENGTH: 41
<212> TYPE: PRT
<213> ORGANISM: Artificial Sequence
<220> FEATURE:
<223> OTHER INFORMATION: Synthetic peptide used to assemble D-eboIZN39IQ
```

<400> SEQUENCE: 6

Cys Ile Asp Phe Leu Leu Gln Arg Met Lys Gln Ile Glu Asp Lys Ile
1               5                   10                  15

Glu Ile Glu Ser Lys Gln Lys Lys Ile Glu Asn Glu Ile Ala Arg
            20                  25                  30

Ile Lys Lys Leu Ile Gly Glu Arg Tyr
        35                  40

<210> SEQ ID NO 7
<211> LENGTH: 26
<212> TYPE: PRT
<213> ORGANISM: Artificial Sequence
<220> FEATURE:
<223> OTHER INFORMATION: Synthetic peptide used to assemble D-eboIZN39IQ
<220> FEATURE:
<221> NAME/KEY: MOD_RES
<222> LOCATION: 1
<223> OTHER INFORMATION: Boc-L-thiazolidine-4-carboxylic acid

<400> SEQUENCE: 7

Asn Glu Thr Thr Gln Ala Leu Gln Leu Phe Leu Arg Ala Thr Thr Glu
1 5 10 15

Leu Arg Thr Phe Ser Ile Leu Asn Arg Lys
20 25

<210> SEQ ID NO 8
<211> LENGTH: 33
<212> TYPE: PRT
<213> ORGANISM: Artificial Sequence
<220> FEATURE:
<223> OTHER INFORMATION: Synthetic peptide used to assemble D-eboIZN39IQ

<400> SEQUENCE: 8

Gly His Met Asp Ile Lys Lys Glu Ile Glu Ala Ile Lys Lys Glu Gln
1 5 10 15

Glu Ala Ile Lys Lys Lys Ile Glu Ala Ile Glu Lys Glu Leu Arg Gln
20 25 30

Leu

<210> SEQ ID NO 9
<211> LENGTH: 90
<212> TYPE: DNA
<213> ORGANISM: Artificial Sequence
<220> FEATURE:
<223> OTHER INFORMATION: forward eboC37 oligonucleotide

<400> SEQUENCE: 9
atgcggtacc tttctattct cattcttggg gcggcacctg ccatattctg ggcccggatt 60
gcgcgattga accgcatgat tggaccaaaa 90

<210> SEQ ID NO 10
<211> LENGTH: 90
<212> TYPE: DNA
<213> ORGANISM: Artificial Sequence
<220> FEATURE:
<223> OTHER INFORMATION: Reverse eboC37 oligonucleotide

<400> SEQUENCE: 10
ccttttcggc cgaaccccca cctttatcca caaaatcatg aataatctga tcaattttat 60
cggtaatgtt tttggtccaa tcatgcggtt 90

```
<210> SEQ ID NO 11
<211> LENGTH: 60
<212> TYPE: DNA
<213> ORGANISM: Artificial Sequence
<220> FEATURE:
<223> OTHER INFORMATION: Forward eboC24 oligonucleotide

<400> SEQUENCE: 11
atgcggtacc tttctattct cattctattg aaccgcatga ttggaccaaa aacattaccg        60

<210> SEQ ID NO 12
<211> LENGTH: 90
<212> TYPE: DNA
<213> ORGANISM: Artificial Sequence
<220> FEATURE:
<223> OTHER INFORMATION: Reverse eboC24 oligonucleotide

<400> SEQUENCE: 12 cctttttcggc cgaaccccca cctttatcca caaaatcatg aataatctga tcaattttat       60
cggtaatgtt tttggtccaa tcatgcggtt                                         90

<210> SEQ ID NO 13
<211> LENGTH: 39
<212> TYPE: PRT
<213> ORGANISM: Ebolavirus Zaire

<400> SEQUENCE: 13

Leu Arg Gln Leu Ala Asn Glu Thr Thr Gln Ala Leu Gln Leu Phe Leu
  1               5                  10                  15

Arg Ala Thr Thr Glu Leu Arg Thr Phe Ser Ile Leu Asn Arg Lys Ala
             20                  25                  30

Ile Asp Phe Leu Leu Gln Arg
         35

<210> SEQ ID NO 14
<211> LENGTH: 39
<212> TYPE: PRT
<213> ORGANISM: Ebolavirus Tai Forest

<400> SEQUENCE: 14

Leu Arg Gln Leu Ala Asn Glu Thr Thr Gln Ala Leu Gln Leu Phe Leu
  1               5                  10                  15

Arg Ala Thr Thr Glu Leu Arg Thr Phe Ser Ile Leu Asn Arg Lys Ala
             20                  25                  30

Ile Asp Phe Leu Leu Gln Arg
         35

<210> SEQ ID NO 15
<211> LENGTH: 39
<212> TYPE: PRT
<213> ORGANISM: Ebolavirus Bundibugyo

<400> SEQUENCE: 15

Leu Arg Gln Leu Ala Asn Glu Thr Thr Gln Ala Leu Gln Leu Phe Leu
  1               5                  10                  15

Arg Ala Thr Thr Glu Leu Arg Thr Phe Ser Ile Leu Asn Arg Lys Ala
             20                  25                  30

Ile Asp Phe Leu Leu Gln Arg
         35
```

<210> SEQ ID NO 16
<211> LENGTH: 39
<212> TYPE: PRT
<213> ORGANISM: Ebolavirus Sudan

<400> SEQUENCE: 16

Leu Arg Gln Leu Ala Asn Glu Thr Thr Gln Ala Leu Gln Leu Phe Leu
 1               5                  10                  15

Arg Ala Thr Thr Glu Leu Arg Thr Tyr Thr Ile Leu Asn Arg Lys Ala
            20                  25                  30

Ile Asp Phe Leu Leu Arg Arg
        35

<210> SEQ ID NO 17
<211> LENGTH: 39
<212> TYPE: PRT
<213> ORGANISM: Ebolavirus Reston

<400> SEQUENCE: 17

Leu Arg Gln Leu Ala Asn Glu Thr Thr Gln Ala Leu Gln Leu Phe Leu
 1               5                  10                  15

Arg Ala Thr Thr Glu Leu Arg Thr Tyr Ser Leu Leu Asn Arg Lys Ala
            20                  25                  30

Ile Asp Phe Leu Leu Gln Arg
        35

<210> SEQ ID NO 18
<211> LENGTH: 39
<212> TYPE: PRT
<213> ORGANISM: Marburgvirus

<400> SEQUENCE: 18

Leu Arg Arg Leu Ala Asn Gln Thr Ala Lys Ser Leu Glu Leu Leu Leu
 1               5                  10                  15

Arg Val Thr Thr Glu Glu Arg Thr Phe Ser Leu Ile Asn Arg His Ala
            20                  25                  30

Ile Asp Phe Leu Leu Thr Arg
        35

<210> SEQ ID NO 19
<211> LENGTH: 39
<212> TYPE: PRT
<213> ORGANISM: Cuevavirus

<400> SEQUENCE: 19

Leu Arg Glu Leu Ala Asn Thr Thr Thr Lys Ala Leu Gln Leu Phe Leu
 1               5                  10                  15

Arg Ala Thr Thr Glu Glu Arg Thr Phe Ser Leu Ile Asn Arg His Ala
            20                  25                  30

Ile Asp Phe Leu Leu Thr Arg
        35

<210> SEQ ID NO 20
<211> LENGTH: 37
<212> TYPE: PRT
<213> ORGANISM: Artificial Sequence
<220> FEATURE:
<223> OTHER INFORMATION: Ebolavirus Zaire, C-peptide

```
<400> SEQUENCE: 20

Trp Gly Gly Thr Cys His Ile Leu Gly Pro Asp Cys Ala Ile Glu Pro
1               5                   10                  15

His Asp Trp Thr Lys Asn Ile Thr Asp Lys Ile Asp Gln Ile Ile His
            20                  25                  30

Asp Phe Val Asp Lys
            35

<210> SEQ ID NO 21
<211> LENGTH: 48
<212> TYPE: PRT
<213> ORGANISM: Artificial Sequence
<220> FEATURE:
<223> OTHER INFORMATION: N-trimer mimic eboIZN21

<400> SEQUENCE: 21

Tyr Gly Ile Lys Lys Glu Ile Glu Ala Ile Lys Lys Glu Gln Glu Ala
1               5                   10                  15

Ile Lys Lys Lys Ile Glu Ala Ile Glu Lys Glu Leu Arg Gln Leu Ala
            20                  25                  30

Asn Glu Thr Thr Gln Ala Leu Gln Leu Phe Leu Arg Ala Thr Thr Glu
            35                  40                  45

<210> SEQ ID NO 22
<211> LENGTH: 48
<212> TYPE: PRT
<213> ORGANISM: Artificial Sequence
<220> FEATURE:
<223> OTHER INFORMATION: N-trimer mimic eboIZN21(D2)

<400> SEQUENCE: 22

Tyr Gly Ile Lys Lys Glu Ile Glu Ala Ile Lys Lys Glu Gln Glu Ala
1               5                   10                  15

Ile Lys Lys Lys Ile Glu Ala Ile Glu Lys Glu Leu Arg Gln Leu Ala
            20                  25                  30

Asn Glu Thr Thr Gln Asp Leu Gln Leu Phe Leu Arg Asp Thr Thr Glu
            35                  40                  45

<210> SEQ ID NO 23
<211> LENGTH: 101
<212> TYPE: PRT
<213> ORGANISM: Artificial Sequence
<220> FEATURE:
<223> OTHER INFORMATION: N-trimer mimic eboIZN39IQ

<400> SEQUENCE: 23

Gly His Met Asp Ile Lys Lys Glu Ile Glu Ala Ile Lys Lys Glu Gln
1               5                   10                  15

Glu Ala Ile Lys Lys Ile Glu Ala Ile Glu Lys Glu Leu Arg Gln
            20                  25                  30

Leu Ala Asn Glu Thr Thr Gln Ala Leu Gln Leu Phe Leu Arg Ala Thr
            35                  40                  45

Thr Glu Leu Arg Thr Phe Ser Ile Leu Asn Arg Lys Ala Ile Asp Phe
50                  55                  60

Leu Leu Gln Arg Met Lys Gln Ile Glu Asp Lys Ile Glu Glu Ile Glu
65                  70                  75                  80

Ser Lys Gln Lys Lys Ile Glu Asn Glu Ile Ala Arg Ile Lys Lys Leu
                85                  90                  95

Ile Gly Glu Arg Tyr
            100
```

```
<210> SEQ ID NO 24
<211> LENGTH: 101
<212> TYPE: PRT
<213> ORGANISM: Artificial Sequence
<220> FEATURE:
<223> OTHER INFORMATION: N-trimer mimic eboIZN39IQ(D3)

<400> SEQUENCE: 24

Gly His Met Asp Ile Lys Lys Glu Ile Glu Ala Ile Lys Lys Glu Gln
  1               5                  10                  15

Glu Ala Ile Lys Lys Lys Ile Glu Ala Ile Glu Lys Glu Leu Arg Gln
             20                  25                  30

Leu Ala Asn Glu Thr Thr Gln Asp Leu Gln Leu Phe Leu Arg Asp Thr
         35                  40                  45

Thr Glu Leu Arg Thr Phe Ser Ile Leu Asn Arg Lys Asp Ile Asp Phe
 50                  55                  60

Leu Leu Gln Arg Met Lys Gln Ile Glu Asp Lys Ile Glu Glu Ile Glu
 65                  70                  75                  80

Ser Lys Gln Lys Lys Ile Glu Asn Glu Ile Ala Arg Ile Lys Lys Leu
                 85                  90                  95

Ile Gly Glu Arg Tyr
            100

<210> SEQ ID NO 25
<211> LENGTH: 33
<212> TYPE: PRT
<213> ORGANISM: Artificial Sequence
<220> FEATURE:
<223> OTHER INFORMATION: N-terminal peptide
<220> FEATURE:
<221> NAME/KEY: MOD_RES
<222> LOCATION: 1
<223> OTHER INFORMATION: Biotin

<400> SEQUENCE: 25

Gly His Met Asp Ile Lys Lys Glu Ile Glu Ala Ile Lys Lys Glu Gln
  1               5                  10                  15

Glu Ala Ile Lys Lys Lys Ile Glu Ala Ile Glu Lys Glu Leu Arg Gln
             20                  25                  30

Leu

<210> SEQ ID NO 26
<211> LENGTH: 26
<212> TYPE: PRT
<213> ORGANISM: Artificial Sequence
<220> FEATURE:
<223> OTHER INFORMATION: middle peptide
<220> FEATURE:
<221> NAME/KEY: MOD_RES
<222> LOCATION: 1
<223> OTHER INFORMATION: Boc-L-thiazolidine-4-carboxylic acid (THZ)

<400> SEQUENCE: 26

Asn Glu Thr Thr Gln Ala Leu Gln Leu Phe Leu Arg Ala Thr Thr Glu
  1               5                  10                  15

Leu Arg Thr Phe Ser Ile Leu Asn Arg Lys
             20                  25

<210> SEQ ID NO 27
<211> LENGTH: 41
<212> TYPE: PRT
<213> ORGANISM: Artificial Sequence
<220> FEATURE:
<223> OTHER INFORMATION: C-terminal peptide
```

```
<400> SEQUENCE: 27

Cys Ile Asp Phe Leu Leu Gln Arg Met Lys Gln Ile Glu Asp Lys Ile
1               5                   10                  15

Glu Glu Ile Glu Ser Lys Gln Lys Lys Ile Glu Asn Glu Ile Ala Arg
            20                  25                  30

Ile Lys Lys Leu Ile Gly Glu Arg Tyr
        35                  40

<210> SEQ ID NO 28
<211> LENGTH: 67
<212> TYPE: PRT
<213> ORGANISM: Artificial Sequence
<220> FEATURE:
<223> OTHER INFORMATION: ligated middle peptide and C-terminal peptide
<220> FEATURE:
<221> NAME/KEY: MOD_RES
<222> LOCATION: 1
<223> OTHER INFORMATION: Boc-L-thiazolidine-4-carboxylic acid (THZ)

<400> SEQUENCE: 28

Asn Glu Thr Thr Gln Ala Leu Gln Leu Phe Leu Arg Ala Thr Thr Glu
1               5                   10                  15

Leu Arg Thr Phe Ser Ile Leu Asn Arg Lys Cys Ile Asp Phe Leu Leu
            20                  25                  30

Gln Arg Met Lys Gln Ile Glu Asp Lys Ile Glu Glu Ile Glu Ser Lys
        35                  40                  45

Gln Lys Lys Ile Glu Asn Glu Ile Ala Arg Ile Lys Lys Leu Ile Gly
    50                  55                  60

Glu Arg Tyr
65

<210> SEQ ID NO 29
<211> LENGTH: 101
<212> TYPE: PRT
<213> ORGANISM: Artificial Sequence
<220> FEATURE:
<223> OTHER INFORMATION: D-eboIZN39IQ
<220> FEATURE:
<221> NAME/KEY: MOD_RES
<222> LOCATION: 1
<223> OTHER INFORMATION: Biotin

<400> SEQUENCE: 29

Gly

```
<210> SEQ ID NO 30
<211> LENGTH: 21
<212> TYPE: PRT
<213> ORGANISM: Artificial Sequence
<220> FEATURE:
<223> OTHER INFORMATION: Ebolavirus N-peptide fragment

<400> SEQUENCE: 30

Leu Arg Gln Leu Ala Asn Glu Thr Thr Gln Ala Leu Gln Leu Phe Leu
  1               5                  10                  15

Arg Ala Thr Thr Glu
             20

<210> SEQ ID NO 31
<211> LENGTH: 32
<212> TYPE: PRT
<213> ORGANISM: Artificial Sequence
<220> FEATURE:
<223> OTHER INFORMATION: IQ peptide

<400> SEQUENCE: 31

Met Lys Gln Ile Glu Asp Lys Ile Glu Glu Ile Glu Ser Lys Gln Lys
  1               5                  10                  15

Lys Ile Glu Asn Glu Ile Ala Arg Ile Lys Lys Leu Ile Gly Glu Arg
             20                  25                  30

<210> SEQ ID NO 32
<211> LENGTH: 25
<212> TYPE: PRT
<213> ORGANISM: Artificial Sequence
<220> FEATURE:
<223> OTHER INFORMATION: IZ peptide

<400> SEQUENCE: 32

Ile Lys Lys Glu Ile Glu Ala Ile Lys Lys Glu Gln Glu Ala Ile Lys
  1               5                  10                  15

Lys Lys Ile Glu Ala Ile Glu Lys Glu
             20                  25
```

EBOLAVIRUS PRE-HAIRPIN INTERMEDIATE MIMICS AND METHODS OF USE

STATEMENT OF GOVERNMENT INTEREST

This invention was made with government support under Grant No. AI102347 awarded by National Institutes of Health, Grant No. GM82545 awarded by National Institutes of Health. The government has certain rights in this invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690181_403WO_SEQUENCE_LISTING.txt. The text file is 13.5 KB, was created on Sep. 23, 2015, and is being submitted electronically via EFS-Web.

BACKGROUND

*Ebolavirus* is an enveloped, negative-strand RNA virus that causes severe hemorrhagic fever(1). Since its identification in 1976, there have been over 20 reported natural *ebolavirus* outbreaks, the majority since 2000, and several accidental laboratory exposures with an overall mortality rate approaching 70%(2). Alarmingly, in 2014 the largest known outbreak is occurring in western Africa (3) and has crossed international borders. Currently, no vaccines or therapeutics are FDA approved. Because of ease of transmission, high mortality, and potential for a severe impact on public health, the CDC places *ebolavirus* in its highest category of potential agents of bioterrorism (4).

There are five known species of *ebolavirus*, four of which are pathogenic to humans. The vast majority of promising preventative and therapeutic candidates with efficacy against *ebolavirus* in animal models, such as vaccines, antibodies, and antisense compounds (e.g., (18-22)), are species-specific, resulting in limited breadth and difficulty in combating emerging species. A vital need remains for a preventative and/or therapeutic to protect against future natural, accidental or deliberate *ebolavirus* outbreaks. The present disclosure provides approaches and embodiments addressing such needs and further provides other related advantages.

BRIEF SUMMARY

Embodiment 1

An *Ebolavirus* N-trimer mimic as described herein.

Embodiment 2

An *Ebolavirus* N-trimer mimic comprising a trimer of monomers, wherein each monomer comprises an *Ebolavirus* glycoprotein 2 (GP2) N-peptide sequence or a portion thereof and at least one soluble trimeric coiled-coil peptide.

Embodiment 3

The *Ebolavirus* N-trimer mimic of embodiment 1, wherein the GP2 N-peptide sequence is any one of SEQ ID NOS:13-17 or a portion thereof.

Embodiment 4

The *Ebolavirus* N-trimer mimic of embodiment 1, wherein the GP2 N-peptide sequence is SEQ ID NO:30.

Embodiment 5

The *Ebolavirus* N-trimer mimic of any one of embodiments 2-4, wherein the at least one soluble trimeric coiled-coil peptide is an IZ peptide (IKKEIEAIKKEQEAIKK-KIEAIEKE, SEQ ID NO:32).

Embodiment 6

The *Ebolavirus* N-trimer mimic of any one of embodiments 2-5, wherein the at least one soluble trimeric coiled-coil peptide is fused to the N-terminus, C-terminus, or both the N-terminus and C-terminus of the N-peptide sequence.

Embodiment 7

The *Ebolavirus* N-trimer mimic of claim 3, further comprising a second soluble trimeric coiled-coil peptide that is an IQ peptide (MKQIEDKIEEIESKQKKIENEIARIK-KLIGER, SEQ ID NO:31).

Embodiment 8

The *Ebolavirus* N-trimer mimic of embodiment 7, wherein the IZ peptide is fused to the N-terminus and the IQ peptide is fused to the C-terminus.

Embodiment 9

The *Ebolavirus* N-trimer mimic of any one of embodiments 2-8, wherein the N-trimer mimic is a homotrimer.

Embodiment 10

The *Ebolavirus* N-trimer mimic of embodiment 2, wherein the *Ebolavirus* N-trimer mimic is eboIZN39IQ, comprising a homotrimer of a monomer comprising a sequence of SEQ ID NO:23.

Embodiment 11

The *Ebolavirus* N-trimer mimic of embodiment 2, wherein the *Ebolavirus* N-trimer mimic is eboIZN21, comprising a homotrimer of a monomer comprising a sequence of SEQ ID NO:21.

Embodiment 12

The *Ebolavirus* N-trimer mimic according to any one of embodiments 1-11, further comprising a pharmaceutically acceptable carrier.

Embodiment 13

A method of inhibiting *Ebolavirus* entry, the method comprising administering an *Ebolavirus* N-trimer mimic of any one of embodiments 1-12 to a subject at risk of exposure to *Ebolavirus*.

Embodiment 14

A method of inhibiting *Ebolavirus* entry into a cell exposed to *Ebolavirus*, the method comprising delivering an

*Ebolavirus* N-trimer mimic of any one of embodiments 1-12 to the cell exposed to *Ebolavirus*.

Embodiment 15

The method of embodiment 13, wherein the subject is human.

Embodiment 16

The method of embodiment 14, wherein the cell is in a human.

Embodiment 17

A method for identifying an inhibitor of *Ebolavirus* entry to a host cell, the method comprising: providing one or more potential ligands; providing an *Ebolavirus* N-trimer mimic according to any one of embodiments 1-12; contacting the *Ebolavirus* N-trimer mimic with each of the one or more potential ligands; and identifying each of the one or more potential ligands that binds the *Ebolavirus* N-trimer mimic.

Embodiment 18

A method according to embodiment 17, wherein providing the *Ebolavirus* N-trimer mimic comprises providing an *Ebolavirus* N-trimer mimic selected from eboIZN39IQ and eboIZN21.

Embodiment 19

A method according to any one of embodiments 17 and 18, wherein providing one or more potential ligands comprises providing a library of potential ligands.

Embodiment 20

The method according to embodiment 19, wherein the library of potential ligands comprises a phage display library.

Embodiment 21

The method of embodiment 20, wherein the *Ebolavirus* N-trimer mimic is synthesized from D-amino acids to provide a D-target and the one or more potential ligands comprise one or more L-peptides.

Embodiment 22

The method of embodiment 21, wherein the method comprises: contacting the D-target with each of the one or more L-peptides; and identifying each of the one or more L-peptides that binds the D-target.

BRIEF DESCRIPTION OF THE SEVERAL VIEWS OF THE DRAWINGS

FIGS. 9A-B: Inhibition of filovirus entry by eboIZN39IQ. (A) A representative pseudovirion assay looking at the inhibitory activity of eboIZN39IQ and the negative control, eboIZN39IQ(D3) against *ebolavirus*, *marburgvirus* and VSV retroviral pseudotypes. Each point represents the average of quadruplicate measurements normalized to uninhibited control. Error bars represent normalized standard errors. For this particular assay, eboIZN39IQ IC50s are 260 nM against *ebolavirus* and 5.4 µM against *marburgvirus*. The eboIZN39IQ(D3) IC50s are 8.9 µM against *ebolavirus* and 11 µM against *marburgvirus*. (B) Data for the authentic filovirus immunofluorescence inhibition assay. Each point represents the average of quadruplicate measurements normalized to vehicle control. Strong inhibition of *ebolavirus* is seen at 10 µM eboIZN39IQ, with an average 33% (+/−4%) of infected cells compared to vehicle control.

FIGS. 15A-C: Synthesis of D-eboIZN39IQ. (A) D-eboIZN39IQ (101aa, with N-terminal biotin, SEQ ID NO:29) was assembled from fragments (SEQ ID NOS: 25-27) using native chemical ligation and metal-free desulfurization. The native alanines and the residues used to replace them for native chemical ligation are indicated (underlined). (B) HPLC analysis of final purified product D-eboIZN39IQ, using XBridge BEH130 C18 column, 2.1× 50 mm, 5 to 90% acetonitrile gradient over 14 min, (C) MS validation showing final product with correct mass.

DETAILED DESCRIPTION

Figure 1:
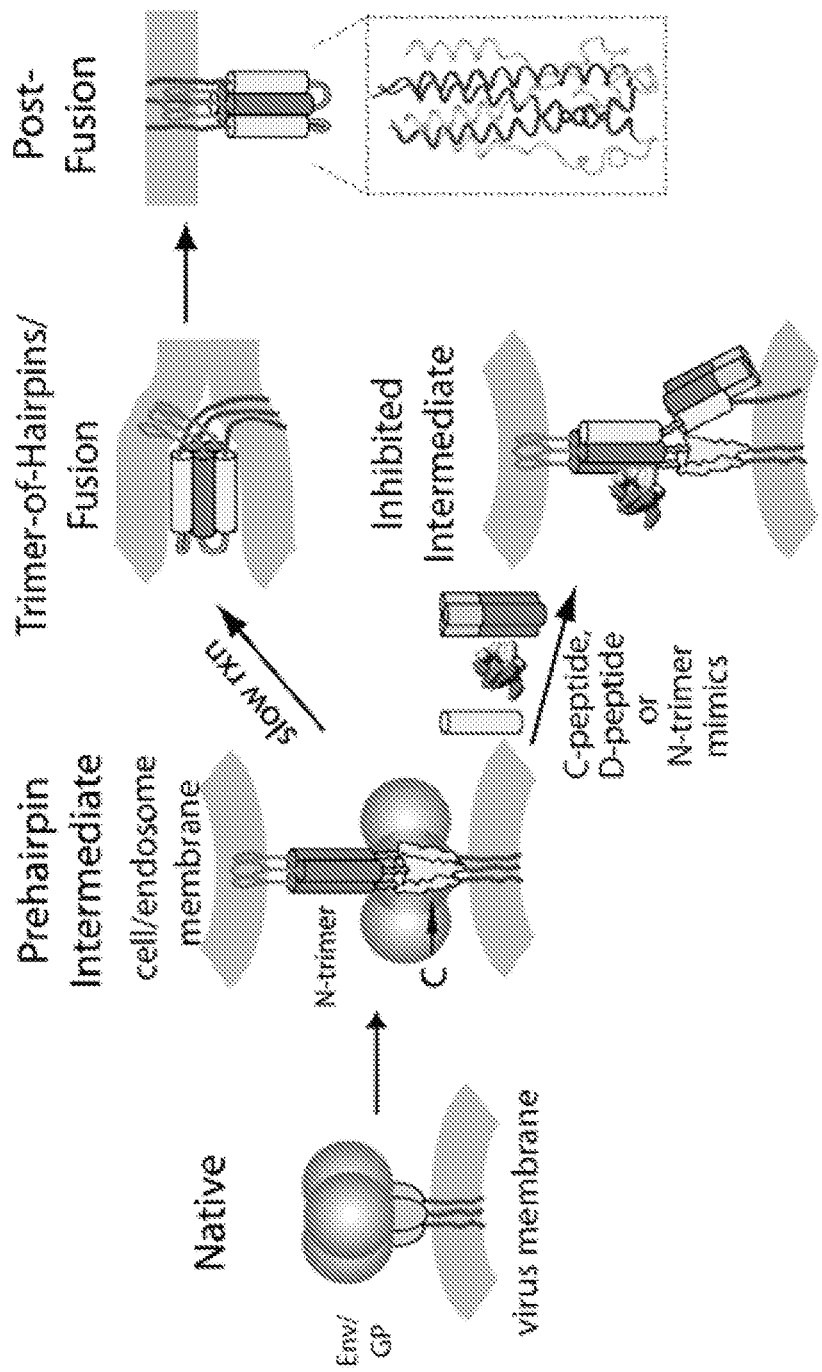
FIG. 1: Model for membrane fusion mediated by enveloped virus surface glycoproteins. The HIV-1 and *ebolavirus* entry events are predicted to be highly similar. First, the surface glycoprotein (Env for HIV-1, glycoprotein (GP) for *ebolavirus*) facilitates viral attachment to the cell and, for *ebolavirus*, the virus is endocytosed and then cleaved by endosomal proteases. Engagement of the virus receptors (CD4 and a chemokine receptor for HIV-1, NPC1 for *ebolavirus*) is followed by a conformational change in Env/GP, and insertion of the fusion peptide/loop (brown) into the host cell membrane. At this stage, the virus is in a transient state that bridges both membranes, termed the "prehairpin intermediate." It is now vulnerable to inhibitors that bind the prehairpin intermediate and inhibit entry. In the absence of an inhibitor, the Env/GP structure slowly resolves into the highly stable trimer-of-hairpins structure, juxtaposing the two membranes and leading to membrane fusion. The inset shows the high resolution structure of the *ebolavirus* trimer-of-hairpins (PDB: 2EBO)(27).

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. The term "consisting essentially of" limits the scope of a claim to the specified materials or steps, or to those that do not materially affect the basic and novel characteristics of the claimed invention. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

The term "Ebolavirus", as used herein, refers to a genus of viruses in the family Filoviridae, order Mononegavirales. Ebolavirus refers to any one or more or all of the five known Ebolavirus species: Zaire, Tai Forest, Bundibugyo, Sudan, and Reston. In certain embodiments, Ebolavirus refers to Ebolavirus Zaire.

The term "N-peptide", as used herein, refers to the N-terminal region (N-trimer) of an Ebolavirus GP2 protein (amino acids 558-596 of FIG. 2A; any one of SEQ ID NOS: 13-17) or any portion thereof. In certain embodiments, a portion of the N-peptide is an N-terminal portion (e.g., SEQ ID NO:30).

The term "N-trimer mimic", as used herein, refers to a trimer of a synthetic peptide comprising at least a portion of the Ebolavirus GP2 protein N-trimer. An N-trimer mimic may be a homotrimer or a heterotrimer. An N-trimer mimic may comprise the entire amino acid sequence of the N-trimer region of Ebolavirus GP2 protein (e.g., having an amino acid sequence of any one of SEQ ID NOS: 13-19) or any portion thereof (e.g., having an amino acid sequence of LRQLANETTQALQLFLRATTE (SEQ ID NO: 30)). An N-trimer mimic may be composed L-peptides, D-peptides, or a combination thereof. In certain embodiments, the N-trimer mimic may be composed entirely of D-amino acids. In some embodiments, the N-trimer mimic may be composed of D-amino acids except for one L-residue (e.g., lysine) on each monomer to allow proteolytic cleavage (e.g., trypsin) of the N-trimer mimic (e.g., for elution during mirror image phage display library screening). The L-residues may be positioned at the N-terminus or C-terminus of the N-trimer mimic.

The term "D-amino acid residue", as used herein, refers to an α-amino acid residue having the same absolute configuration as D-glyceraldehyde. When the amino acid residue includes a first non-hydrogen α-substituent and a second asubstituent selected from methyl and halogen, the absolute configuration is the same as that of D-glyceraldehyde with the second α substituent taking the place of the hydrogen atom at the glyceraldehyde α-carbon.

The term "D-peptide," as used herein, refers to peptide composed of D-amino acid residues.

The term "host cell," as used herein, refers to cells of human or non-human primates.

By "inhibit Ebolavirus entry" is meant a reduction in the number of Ebolavirus particles that are capable of entering a cell. It can mean complete inhibition, in other words no viral particles are capable of entering a cell, or it can mean a partial inhibition, meaning that in a given system there is a reduction in the number of viral particles capable of entering a cell when compared with a non-treated system, or a control. There can be a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96, 97%, 98%, 99%, or 100% reduction in the number of viral particles that are capable of entering a cell, or any amount greater, less, or in between these amounts.

Figure 2A:
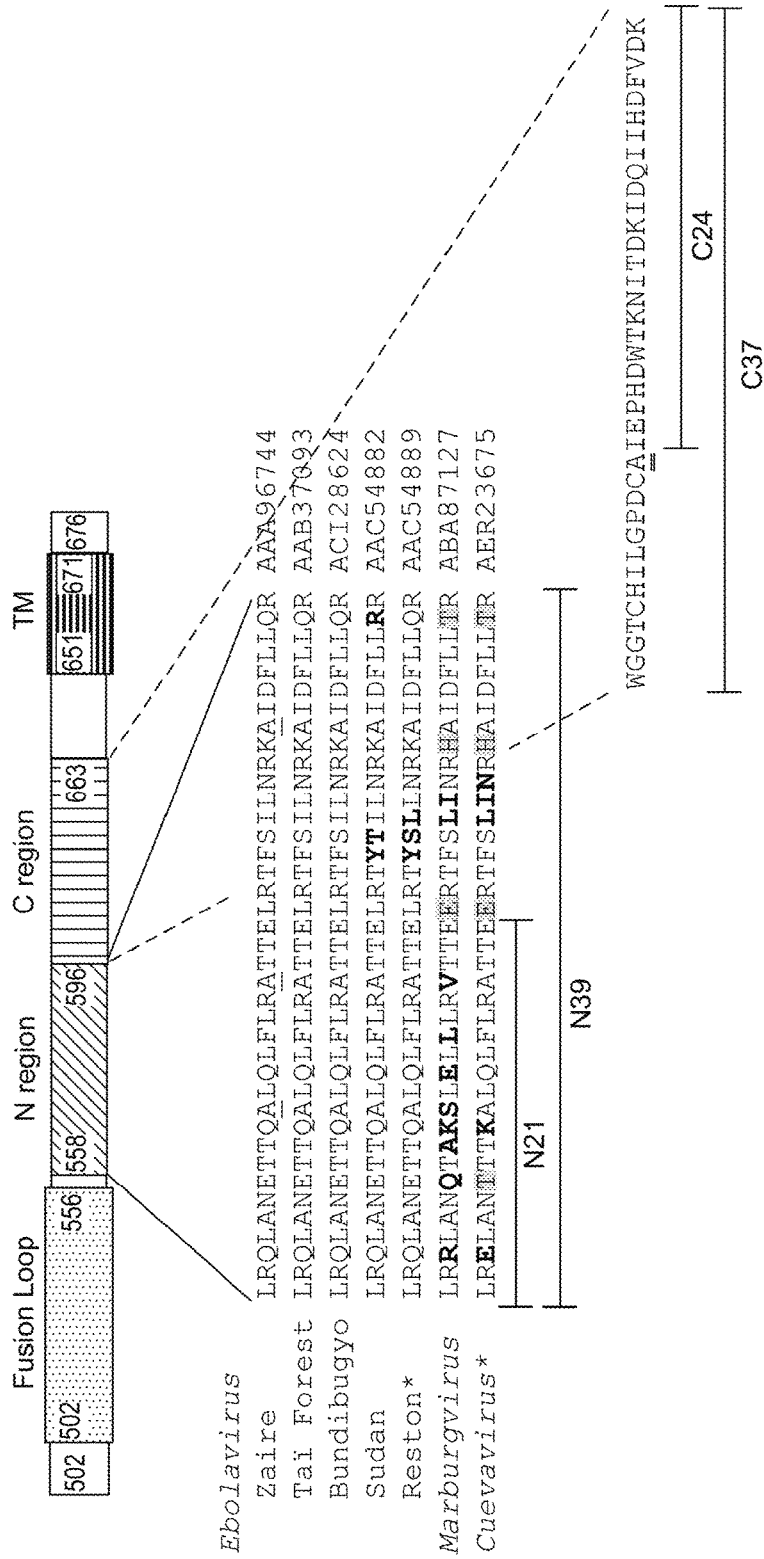
FIGS. 2A-B: Conservation of the *ebolavirus* GP N-trimer and design of peptide N-trimer mimics. (A) Schematic of the primary structure of *ebolavirus* GP2, indicating the fusion loop (dotted), N-trimer (diagnol lines), C-peptide (vertical lines), and transmembrane domain (TM, horizontal lines), all shown approximately to scale. The sequences of the N-trimer region (residues 558-596)(SEQ ID NOS:13-19) and the C-peptide region (SEQ ID NO: 20) (residues 597-633) (*Zaire ebolavirus* species, representative strain isolated in Mayinga, Zaire in 1976(58)) contained in the peptides described in this study are indicated. The N-trimer alanines that are mutated to aspartate in the binding site mutants are indicated (underlined). In the C-peptide, cysteine 609, which is proposed to disulfide bond with GP1(73), is mutated to alanine in our constructs (redouble underlined). Below the Zaire N-trimer is an alignment of the sequences from the 4 additional *ebolavirus* species plus *Marburgvirus* and *Cuevavirus* filoviruses (SEQ ID NOS: 13-19), respectively. Genbank accession codes are indicated (right). Conserved residues (score of 0 or higher in BLOSUM62 matrix(74)) are in bold, non-conserved are highlighted in gray. Notably, ⅗ and ⅘ *ebolavirus* species are 100% identical in our representative Zaire N39 and N21 regions, respectively. The 2014 epidemic is caused by a Zaire species *ebolavirus*, and is therefore 100% identical in this region(3). *Reston and likely *Cuevavirus* are not pathogenic to humans. (B) Schematics and sequences of the N-trimer mimics and their corresponding binding site mutants (eboIZN21 (SEQ ID NO: 21) and eboIZN21(D2) (SEQ ID NO: 22); eboIZN39IQ (SEQ ID NO: 23) and eboIZN39IQ(D3) (SEQ ID NO: 24)). The designed coiled coils, IZm and IQ, are shown in white and gray cross-hatching, while the *ebolavirus* N-trimer is shown in black and white cross-hatching. The a and d positions of the coiled-coil heptad repeats are indicated by a larger font, including a stutter at the N-terminal end of the *ebolavirus* N-trimer as seen in the crystal structures(26; 27), where the coil is underwound, leading to an atypical 3-4-4-3 pattern (instead of the standard 3-4, or a-g, periodicity of a heptad repeat). The alanine residues along the C-peptide binding groove that are mutated to aspartate in the binding site mutants are shown (underlined).

The inventors determined that the N-trimer of the pre-hairpin intermediate is a highly conserved region the Ebolavirus GP2 fusion protein and provides a highly conserved target for potential broad-spectrum inhibitors. Indeed, although the overall sequence identity of GP across all known ebolavirus species is only 42%, the N-peptide region is 90% identical and all changes are conservative (FIG. 2A).

The design, biophysical characterization, and validation of peptide mimics of the *ebolavirus* N-trimer ("N-trimer mimics") are described herein.

In certain embodiments, the N-trimer mimics described herein may be used as inhibitors of *ebolavirus* entry. In further embodiments, the N-trimer mimics described herein may be used as targets to develop broad-spectrum inhibitors of *ebolavirus* entry. In certain such embodiments, the N-trimer mimics may be used to screen small molecule, antibody, and peptide libraries for entry inhibitors that target this highly conserved region. As described herein, peptide mimics of *ebolavirus* N-trimers have been designed and characterized, their use as drug discovery tools was validated, and conditions that can be applied directly to phage display drug discovery endeavors were explored. In addition, through use of an N-trimer mimic according to the present description, the vulnerability of the *ebolavirus* GP prehairpin intermediate to entry inhibition has been demonstrated.

The N-trimer region of GP2 is 90% identical across all *ebolavirus* species and forms a critical part of the prehairpin intermediate that is exposed during viral entry. In particular embodiments, designed coiled coils were fused to the N-trimer to present it as a soluble trimeric coiled coil as it appears during membrane fusion. Circular dichroism, sedimentation equilibrium and x-ray crystallography analyses demonstrated the helical, trimeric structure of the designed peptide mimetics (N-trimer mimic). Surface plasmon resonance studies validated N-trimer mimic binding to the native ligand, the C-peptide region of GP2. The longest N-trimer mimic inhibited virus entry, confirming binding of the C-peptide region during viral entry and the presence of a vulnerable prehairpin intermediate. Using phage display as a model system, the suitability of the N-trimer mimics as drug targets was validated.

*Ebolavirus* entry into host cells, a critical step to infection, is mediated by the viral surface glycoprotein (GP), a class I fusion protein. GP comprises two disulfide-linked subunits, one surface exposed (GP1) and one embedded in the viral membrane (GP2)(5; 6). Following binding to host cells via cell surface attachment factors, the virus is endocytosed. Endosomal cysteine proteases, cathepsins B and L, cleave off much of GP1, exposing the binding site for the receptor, endosomal NPC1(7-11). At this point, the fusion mechanism is thought to mimic that of other well characterized viral class I fusion proteins, such as HIV-1 and influenza(12-14) (FIG. 1). GP2 forms a transient conformation ("prehairpin intermediate") embedded in both the virus (via the transmembrane domain) and host cell (via the fusion loop) membranes. This prehairpin intermediate exposes a trimeric coiled coil formed by the N-terminal region (N-trimer) and the C-terminal region (C-peptide). Slow collapse of the intermediate into a highly stable trimer-of-hairpins structure, with the C-peptide binding into the grooves on the N-trimer, juxtaposes the virus and cell membranes, leading to membrane fusion. In *ebolavirus* entry, the low pH of the endosome contributes to the stability of the trimer-of-hairpins (15).

Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular peptide is disclosed in a multimer, and a number of modifications that can be made to a number of molecules including the peptide are discussed, specifically contemplated is each and every combination and permutation of the peptide in the multimer with other peptides in the multimer, as well as the modifications to the peptides that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

N-Trimer Mimics

Disclosed herein are *Ebolavirus* glycoprotein 2 (GP2) N-trimer mimics composed of a trimer of monomers, wherein each monomer comprises an *Ebolavirus* GP2 N-peptide sequence or a portion thereof. In certain embodiments, an N-peptide sequence comprises at least 10, 11, 12, 13, 14, 15, 16, 17, 18, 19, 20, 21, 22, 23, 24, 25, 26, 27, 28, 29, 30, 31, 32, 33, 34, 35, 36, 37, or 38 residues. A monomer of an *Ebolavirus* N-trimer mimic may comprise the entire 39 amino acid sequence of the N-trimer region of *Ebolavirus* GP2 protein (e.g., comprising an amino acid sequence of any one of SEQ ID NOS: 13-19) or any portion thereof (e.g., comprising an amino acid sequence of LRQLANETTQALQLFLRATTE (SEQ ID NO: 30)). An *Ebolavirus* N-trimer mimic may be composed L-peptides, D-peptides, or a combination thereof. In certain embodiments, the N-trimer mimic may be composed entirely of D-amino acids. In some embodiments, the N-trimer mimic may be composed of D-amino acids except for one L-residue (e.g., lysine) on each monomer to allow proteolytic cleavage (e.g., trypsin) of the N-trimer mimic (e.g., for elution during mirror image phage display library screening). The L-residues may be positioned at the N-terminus or C-terminus of the N-trimer mimic.

In certain embodiments, an *Ebolavirus* N-trimer mimic is a homotrimer composed of identical monomers. In other embodiments, an N-trimer mimic is a heterotrimer composed of two identical monomers and a different monomer, or three different monomers.

In certain embodiments, each monomer of the *Ebolavirus* N-trimer mimic is fused to at least one soluble trimeric coiled-coil peptide derived from any protein, provided that when it is in the fusion protein with the *Ebolavirus* component, the *Ebolavirus* N-trimer cavity is presented in such a manner that it is available for binding. Examples of soluble trimeric coiled-coils that may be used include that of GCN4-pIQI (IQ), GCN4-pII, Moloney Murine Leukemia Virus (Mo-MLV) or the ABC heterotrimer. IQN17 (L-form or D-form). For example, an IQ peptide that may be fused to the N-peptide may comprise SEQ ID NO:31. In another embodiment, a soluble trimeric coiled-coil peptide that may be used is an isoleucine zipper (IZ). For example, an IZ peptide that may be fused the N-peptide may comprise SEQ ID NO:32. In another example, an IZ peptide may be fused to one terminus of the N-peptide and an IQ peptide is fused to the other terminus of the N-peptide. The length of the trimeric coiled-coil peptide can be modified based on the N-trimer mimic fusion partner in order to preserve the heptad repeat so that the α-helical structure, stability and trimeric state of the N-trimer mimic is maintained.

The at least one soluble trimeric coiled-coil peptide may be fused to the N-terminus, C-terminus, or both termini of the N-peptide sequence. In certain embodiments, an IZ peptide (e.g., SEQ ID NO:32) is fused to the N-terminus of the N-peptide sequence. In further embodiments, an IQ peptide (e.g., SEQ ID NO:31) is fused to the C-terminus of the N-peptide sequence. In another embodiment, the *Ebolavirus* N-trimer mimic is eboIZN39IQ, comprising a homotrimer of a monomer comprising a sequence of SEQ ID NO:23. In yet another embodiment, the *Ebolavirus* N-trimer mimic is eboIZN39IQ, composed of a homotrimer of a monomer consisting a sequence of SEQ ID NO:23. In yet another embodiment, the *Ebolavirus* N-trimer mimic is eboIZN21, comprising a homotrimer of a monomer comprising a sequence of SEQ ID NO:21. In yet another embodiment, the *Ebolavirus* N-trimer mimic is composed of a homotrimer of a monomer consisting of a sequence of SEQ ID NO:21.

In certain embodiments, the *Ebolavirus* N-trimer mimic is linked to a potency enhancing cargo molecule. A potency enhancing cargo molecule may be cholesterol, sterol, sugar, maltose binding protein, ubiquitin, streptavidin, immunoglobulin domain, keyhole limpet hemacyanin, sperm whale myoovalbumin, bovine pancreatic trypsin inhibitor, green fluorescent protein, gold particle, magnetic particle, agarose bead, lactose bead, fatty acid, a high molecular weight PEG, or serum albumin. The potency enhancing cargo molecule may be linked to the N-peptide with a PEG linker (e.g., $PEG_{12}$, $PEG_{16}$, $PEG_{24}$, $PEG_{25}$, $PEG_{26}$, $PEG_{27}$, $PEG_{28}$, $PEG_{29}$, $PEG_{30}$, $PEG_{31}$, $PEG_{32}$, $PEG_{33}$, $PEG_{34}$, $PEG_{35}$, or $PEG_{36}$). Potency enhancement of D-peptide trimers using cargo molecules has been described in U.S. Patent Publication 2014/0323392 and Francis et al., 2012, Bioconjug. Chem. 23:1252-8 (each of which is incorporated by reference in its entirety).

Peptide Variants

Variants of the peptides that make up the N-trimer mimics disclosed herein are contemplated. Peptide variants and derivatives are well understood to those of skill in the art and in can involve amino acid sequence modifications. Those peptides disclosed herein that can be used to inhibit viral entry can comprise such amino acid sequence modifications. One of skill in the art would be able to readily determine which modifications can be made in order to retain the activity of the peptide.

Analogs of the peptides disclosed herein are also contemplated. These analogs include one or more D-amino acids of the peptidic structure which are substituted with a homologous amino acid such that the properties of the original peptide are maintained. Preferably conservative amino acid substitutions are made at one or more amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g, glycine, asparagine, glutamine, serine, threonine, tyrosine, cysteine), nonpolar side chains (e.g., alanine, valine, leucine, isoleucine, proline, phenylalanine, methionine, tryptophan), branched side chains (e.g., threonine, valine, isoleucine) and aromatic side chains (e.g., tyrosine, phenylalanine, tryptophan, histidine). Non-limiting examples of homologous substitutions that can be made in the peptidic structures of the peptides disclosed herein include substitution of D-phenylalanine with D-tyrosine, D-pyridylalanine or D-homophenylalanine, substitution of D-leucine with D-valine or other natural or non-natural amino acid having an aliphatic side chain and/or substitution of D-valine with D-leucine or other natural or non-natural amino acid having an aliphatic side chain. This is given as an example and is not intended to be limiting. One of skill in the art would be capable of making conservative substitutions to a D-peptide.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

The opposite stereo-isomers of naturally occurring peptides are disclosed, as well as the stereo-isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —CH=CH— (cis and trans), —$COCH_2$—, —CH(OH)$CH_2$—, and —CHH2SO— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int. J. Pept. Prot. Res. 14:177-185 (1979) (—CH2NH—, CH2CH2—); Spatola et al. Life Sci 38:1243-1249 (1986) (—CHH2—S); Hann J. Chem. Soc. Perkin Trans. 1307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appin, EP 45665 CA (1982): 97:39405 (1982) (—CH(OH)$CH_2$—); Holladay et al. Tetrahedron. Lett 24:4401-4404 (1983) (—C(OH)$CH_2$—); and Hruby Life Sci. 31:189-199

(1982) (—CH$_2$—S—); each of which is incorporated herein by reference. A particularly preferred non-peptide linkage is —CH$_2$NH—. It is understood that peptide analogs can have more than one atom between the bond atoms, such as β-alanine, γ-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by proteases and peptidases. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

The present disclosure also provides an isolated composition comprising any of the embodiments of N-trimer mimics disclosed herein.

Pharmaceutical Compositions and Delivery Thereof

The *Ebolavirus* N-trimer mimics disclosed herein (alternatively referred to as compositions) can also be administered in vivo in a pharmaceutically acceptable carrier. By "pharmaceutically acceptable" is meant a material that is not biologically or otherwise undesirable, i.e., the material may be administered to a subject, along with the peptide disclosed herein, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the disease, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The N-trimer mimic compositions can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed peptides and multimers thereof can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Therapeutic Uses

Effective dosages and schedules for administering the N-trimer mimic compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter-indications. Dosage can vary, and can be administered in one or more dose administrations daily, for one or several days. Guidance can be found in the literature for appropriate dosages for given classes of pharmaceutical products, particularly for D-peptides. Examples of such guidance can be found throughout the literature. In one embodiment, the typical daily dosage of the N-trimer mimics thereof used alone might range from about 1 µg/kg to up to 100 mg/kg of body weight or more per day, depending on the factors mentioned above. Furthermore, the peptides disclosed herein can be administered several times daily, daily, weekly, monthly, or yearly, depending on the condition of the subject, other modes of therapy, etc. One of skill in the art could readily ascertain an appropriate dosing schedule.

Following administration of a disclosed composition, such as an N-trimer mimic, for treating, inhibiting, or preventing an *Ebolavirus* infection, the efficacy of the N-trimer mimic thereof can be assessed in various ways well known to the skilled practitioner. For instance, one of ordinary skill in the art will understand that a composition, such as a N-trimer mimic, disclosed herein is efficacious in treating or inhibiting an *Ebolavirus* infection in a subject by observing that the composition inhibits *Ebolavirus* entry. Efficacy of the administration of the disclosed composition may also be determined by measuring the number of uninfected cells in the infected subject. A treatment that inhibits an initial or further decrease in uninfected cells in a subject or patient, or that results in an increase in the number of uninfected cells in, for example, the *Ebolavirus*-positive subject, is an efficacious treatment. The efficacy can also be evaluated using indirect measures of infection, such as, levels of anti-*Ebolavirus* antibodies, and PCR to detect viral RNA levels.

The compositions that inhibit viral entry, i.e., microbicides, disclosed herein may be administered prophylactically to patients or subjects who are at risk for being exposed to a virus such as *Ebolavirus* or who have been newly exposed to *Ebolavirus*. In subjects who have been newly exposed to a virus such as *Ebolavirus* but who have not yet displayed the presence of the virus (as measured by PCR or other assays for detecting the virus) in blood or other body fluid, efficacious treatment with a peptide or multimer thereof partially or completely inhibits the ability of the virus to infect cells.

The disclosed compositions and methods can also be used for example as tools to isolate and test new drug candidates for a variety of viral-related diseases.

Methods of Identifying an Inhibitor of *Ebolavirus* Entry

Also disclosed herein is are methods of identifying an inhibitor of *Ebolavirus* entry, comprising: (a) providing one or more potential ligands, (b) providing an *Ebolavirus* N-trimer mimic according to any of the embodiments disclosed herein, (c) contacting the *Ebolavirus* N-trimer mimic with each of the one or more potential ligands, and (d) identifying each one of the one or more potential ligands that binds to the *Ebolavirus* N-trimer mimic.

In certain embodiments, the one or more potential ligands is selected from a small molecule, antibody, and peptide.

In certain embodiments, the *Ebolavirus* N-trimer mimic provided is selected from eboIZN39IQ and eboIZN21.

In certain embodiments, a library of potential ligands is provided. In certain embodiments, the library of potential ligands is a library of small molecules, antibodies, or peptides.

In certain embodiments, the library of potential ligands comprises a phage display library.

In certain embodiments, the *Ebolavirus* N-trimer mimic is synthesized from D-amino acids to provide a D-target and the one or more potential ligands comprise one or more L-peptides (e.g., mirror-image phage display library screening). Such embodiments may comprise contacting the D-target with each of the one or more L-peptides; and identifying each of the one or more L-peptides that binds the D-target.

The methods of identifying an inhibitor of *Ebolavirus* entry described herein may be repeated one or more times with the library of potential ligands to enrich for ligands that bind to the N-trimer mimic. Selection pressure may be increased in each round of screening, for example by increasing the number and/or length of washes at each subsequent round.

A potential ligand may be detectably labeled and binding of the potential ligand to the N-trimer mimic is determined by detecting the presence of the detectable label on the N-trimer mimic (as a result of binding of the labeled candidate ligand to the N-helix coiled-coil).

Ligands identified using the methods described herein may be subject to further experiments, ELISA, to confirm binding of the ligand to the N-trimer target. Ligands identified by the methods described above may then be further tested for their ability to inhibit (totally or partially) *Ebolavirus* GP2 protein function (membrane fusion) and, thus entry into cells, using further in vitro assays, such as the syncytium assays and/or infectivity assays described herein or others known to those of skill in the art, and/or in vivo assays in appropriate animal models or in humans.

Methods of Inhibiting *Ebolavirus* Entry

The *Ebolavirus* N-trimer mimics, including pharmaceutical compositions thereof, described herein may be used in methods for inhibiting entry of *Ebolavirus* into a cell exposed to *Ebolavirus*, the method comprising administering an *Ebolavirus* N-trimer mimic of any of the embodiments described herein to a subject at risk of exposure to Ebolavirus. Another method of inhibiting Ebolavirus entry into a cell exposed to Ebolavirus comprises administering an Ebolavirus N-trimer mimic of any of the embodiments described herein to the cell exposed to Ebolavirus. An Ebolavirus may be any one of Ebolavirus Zaire, Ebolavirus Tai Forest, Ebolavirus Bundibugyo, Ebolavirus Sudan, Ebolavirus Reston, or any combination thereof. In certain embodiments, an Ebolavirus is Ebolavirus Zaire.

Similarly, the Ebolavirus N-trimer mimics, including pharmaceutical compositions thereof, described herein may be used in methods of treating Ebolavirus infection in a subject who has been exposed to Ebolavirus, comprising administering to the subject a therapeutically effective amount of the N-trimer mimic. A subject in any of the methods described herein may be a human or non-human primate.

The methods disclosed herein can be used in conjunction with other antiviral therapies or antiviral agents. One of more of these antiviral agents can be used, and they can be administered before or after treatment (sequentially), or during treatment (concurrently, in the same or separate formulations) with the compositions disclosed herein. For example, in ongoing therapy, the subject can be administered the compositions comprised herein simultaneously with other treatments, meaning they can be administered about 48 hours, 24 hours, 12 hours, 8 hours, 4 hours, 2 hours, 1 hour, 30 minutes, 20 minutes, 10 minutes, 5 minutes, or one minute before treatment with the disclosed compositions. Other methods of treatment can also be administered before treatment with the compositions disclosed herein. By "before treatment" is meant that another form of treatment was given and then stopped before the current therapy was administered, or could be given immediately before, then administered again afterwards. In this case, the other methods of antiviral therapy can be administered years, months, weeks, days, hours, or minutes in advance. Other methods of treatment can also be administered after treatment with the compositions disclosed herein. By "after treatment" is meant that another form of treatment is administered after the current therapy was administered, or could be given before, then administered again afterwards. This additional antiviral treatment could be given years, months, weeks, days, hours, or minutes after the current therapy is given.

The further antiviral agent or agents can be any one of a viral fusion inhibitor, viral attachment inhibitor, viral replication inhibitor, a viral protease inhibitor, a viral entry inhibitor. An antiviral agent may be an inhibitor antibody, a biologic, an antisense molecule, a ribozyme, an RNA interference agent, a peptide, a vaccine, or a small molecule. Further anti-viral agents include supportive treatment, such as intravenous fluids.

EXAMPLES

Example 1: N-Trimer Mimic Design

Figure 2B:
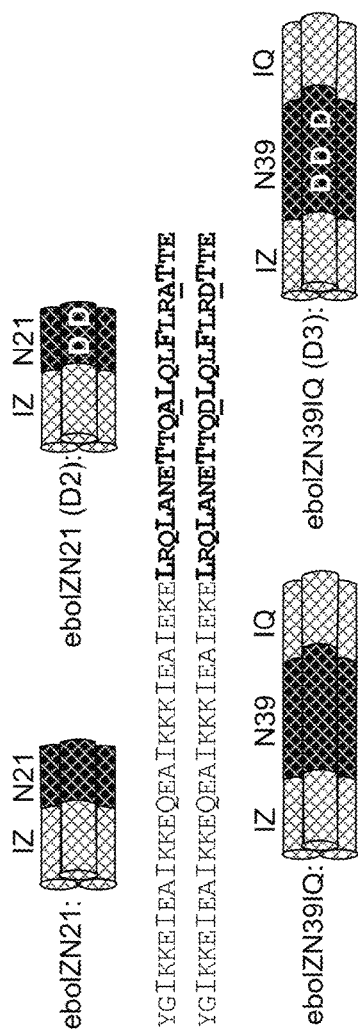

Applicants designed soluble peptide mimics of the N-trimer region of the ebolavirus GP prehairpin intermediate. In designing these peptide mimics, Applicants fused stable, soluble, designed trimeric coiled coils to the N-trimer sequence (FIG. 2B). The ebolavirus N-trimer aggregates when produced in isolation. Applicants were interested in presenting the entire N-trimer groove as well as a smaller, more conserved region of the N-trimer to provide flexibility in targeting and drug screening. The initial designs, in which the isoleucine zipper coiled coil $IZ_m(24)$ was fused to the N-terminus of N-trimer segments of 29 and 39 amino acids, were highly aggregated as determined by analytical ultracentrifugation (AUC) sedimentation equilibrium experiments (data not shown). To overcome this problem, an additional trimeric coiled coil, GCN4-$pI_QI'$ (IQ) (25) (MKQ-IEDKIEEIESKQKKIENEIARIKKLIGER) (SEQ ID NO: 31) was fused to the C-terminus of the Ebolavirus N-trimer segment. The resulting peptide, eboIZN39IQ presents the full Ebolavirus N-trimer (determined from available trimer-of-hairpins crystal structures(26; 27)) as a trimeric coiled coil, as shown by circular dichroism (CD) (FIG. 3A) and AUC (FIG. 3C and Table 1). eboIZN39IQ is highly stable, as it has almost identical CD spectra at 25° C., 37° C. and 50° C. (Table 1). In particular embodiments, an ebolavirus N-trimer as described herein may be used as a target in drug screening to identify inhibitors of ebolavirus entry. Since these inhibitors will bind to the virus in the endosome, all biophysical analyses described herein were performed at pH 5.8 to mimic endosomal pH.

TABLE 1

| Peptide | $[\theta_{222\,nm}]$ (deg cm² dmol⁻¹) 25° C. | $[\theta_{222\,nm}]$ (deg cm² dmol⁻¹) 37° C. | $[\theta_{222\,nm}]$ (deg cm² dmol⁻¹) 50° C. | $M_{obs}/M_{calc}$ 4° C. |
|---|---|---|---|---|
| eboIZN39IQ | −29,400 | −27,900 | −27,100 | 3.24 |
| eboIZN39IQ(D3) | −30,400 | −29,300 | −28,400 | 3.22 |
| eboIZN21 | −25,500 | −24,000 | −22,900 | 3.54 |
| eboIZN21(D2) | −24,800 | −22,800 | −21,800 | 3.15 |

CD scans were performed on the same samples of 11.4 µM eboIZN39IQ, 11.1 µM eboIZN39IQ(D3), 18.0 µM eboIZN21 and 25.3 µM eboIZN21(D2) in 50 mM sodium phosphate, pH 5.8, 150 mM NaCl at 25° C., 37° C., and 50° C. The peptides were allowed to equilibrate at each temperature for 10 minutes, after which no change in signal was seen over time. Sedimentation equilibrium analysis was performed on each peptide at three concentrations each (a starting concentration and two 2-fold dilutions, with typical starting concentrations between 10-30 µM) and a minimum of two speeds, but typically three speeds (18,000, 21,000 and 24,000 RPM). Each data set was globally fit to a single ideal species. Each sedimentation equilibrium analysis was performed 2-4 times and averaged for the above table.

Figure 10:
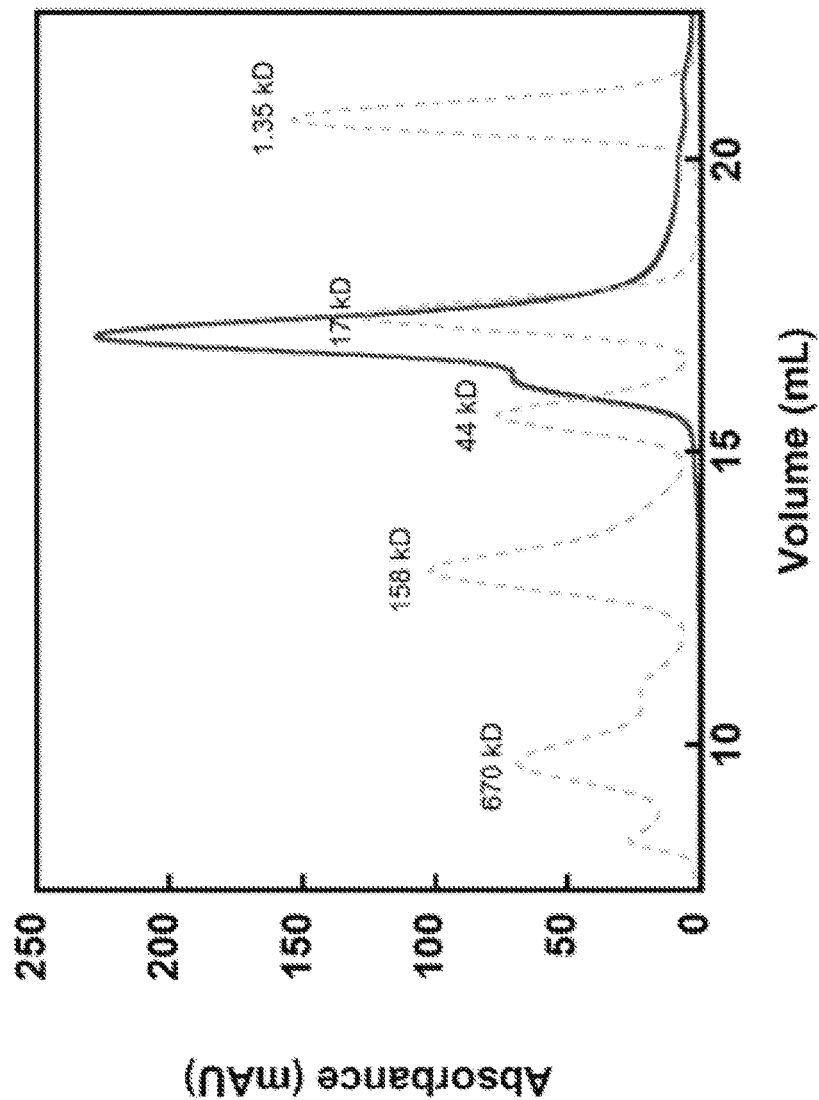
FIG. 10: Gel filtration analysis of 240 µM eboIZN21 (bold line, recorded at 215 nm) in 50 mM sodium phosphate pH 5.8, 100 mM NaCl using a Superdex 200 column on an ÄKTApurifier (GE Healthcare Life Sciences) at room temperature with a 0.5 mL/min flowrate. Gel filtration standards (Bio-Rad) and their molecular weights are overlaid (grey dashed line, recorded at 280 nm). The predominant peak is consistent with a trimer, with a left shoulder containing higher order assemblies.

To produce a smaller target that presents a 100% identical region of the N-trimer (across all ebolavirus species), $IZ_m$ was fused to the N-terminal 21 amino acids of the N-trimer, resulting in eboIZN21 (FIG. 2). Circular dichroism indicated eboIZN21 is highly helical (FIG. 3B), and AUC and gel filtration studies showed it was largely trimeric with a slight tendency to form higher order aggregates (Table 1 and FIG. 10). X-ray crystallography studies confirmed the trimeric coiled-coil structure of eboIZN21 (below). As seen with eboIZN39IQ, eboIZN21 is highly stable, showing almost identical CD spectra at 25° C., 37° C. and 50° C. (Table 1).

Figure 3:
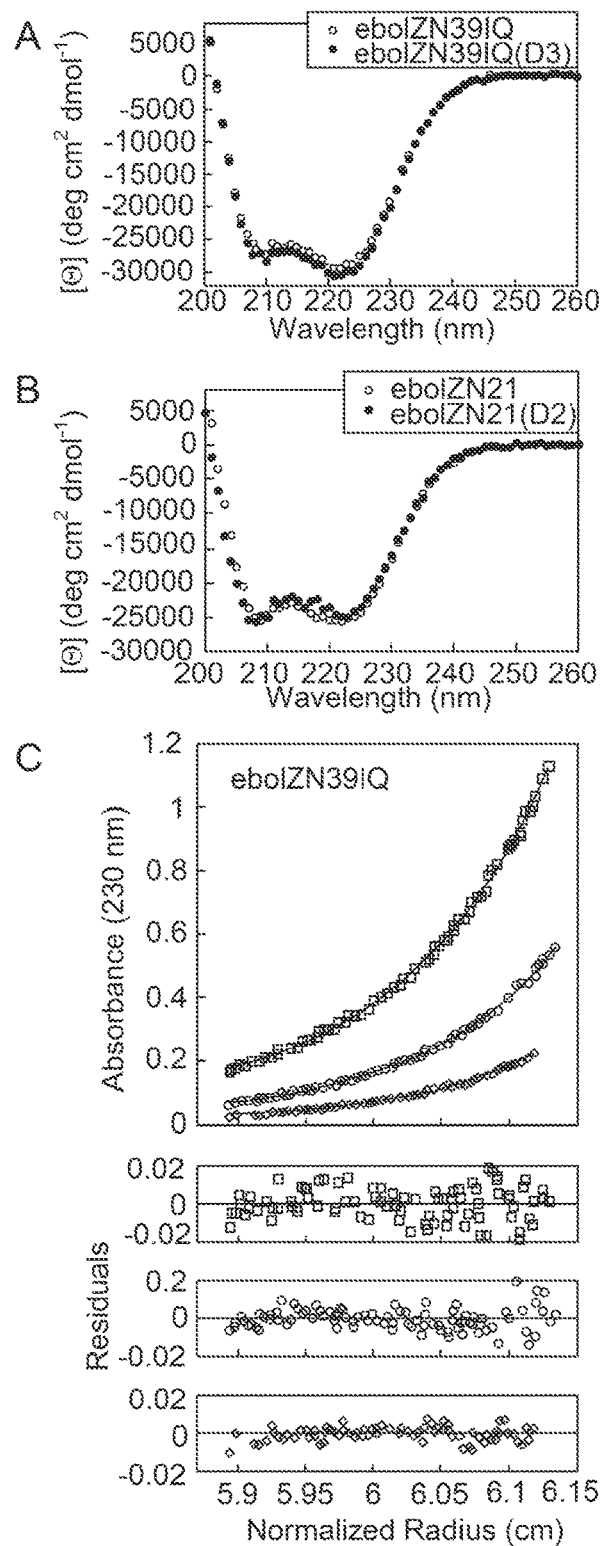
FIGS. 3A-C: Biophysical analyses of *ebolavirus* N-trimer mimics. (A) CD spectra of 11.4 µM eboIZN39IQ and 11.1 µM eboIZN39IQ(D3) at 25° C. Both spectra indicate a highly helical conformation. (B) CD spectra of 18.0 µM eboIZN21 and 25.3 µM eboIZN21(D2) at 25° C., also indicate of a completely helical conformation. (C) Analytical ultracentrifugation (AUC) sedimentation equilibrium analysis of eboIZN39IQ, shown as representative AUC data. 10, 5 and 2.5 µM peptide solutions were centrifuged at 18,000, 21,000 and 24,000 RPM at 4° C. on a Beckman XLA. All data were globally fit to a single ideal species, and an observed molecular weight of 39,762 Da was determined for an Mobs/Mcalc of 3.31. The data (open symbols) and fit (solid lines) are shown for the lowest speed.

As negative controls for binding studies and drug discovery efforts, mutant N-trimer mimics aimed at abolishing the C-peptide binding site were produced. Specifically, alanines that are found along the C-peptide binding groove were mutated to aspartate, introducing likely binding-disruptive charges along the groove (FIG. 2). The resulting peptides were termed eboIZN39IQ(D3) and eboIZN21(D2). Using CD and AUC, it was confirmed that these mutants maintained the highly stable coiled-coil structure and trimeric nature of their wild-type counterparts (FIG. 3 and Table 1).

Example 2: C-Peptide Binding Characterization

Figure 4:
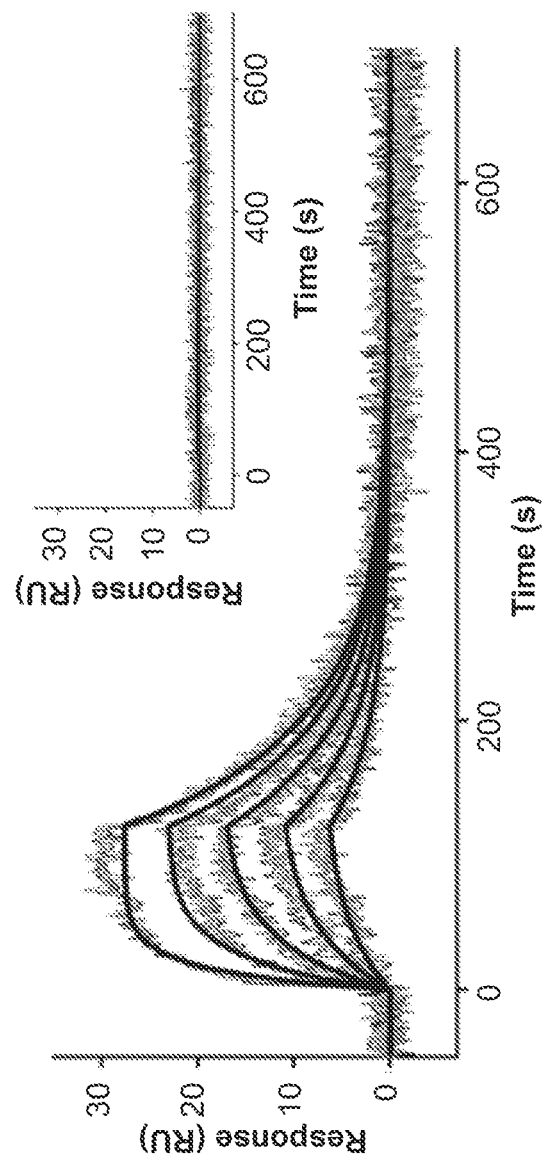
FIG. 4: Binding of the *ebolavirus* C-peptide to the N-trimer mimic. Sensorgram of eboC37 flowed over eboIZN39IQ in a triplicate 2-fold dilution series starting at 60 nM, plotted with 2nd order 2-neighbor-smoothing with a Savitzky-Golay filter (Prism 6, GraphPad Software). Each replicate dilution series is shown as a distinct color. The kinetic fit of the raw data is shown and yields $k_a$=9.6×10$^5$ $M^{-1}s^{-1}$, $k_d$=0.014 $s^{-1}$, and a $K_D$ of 14 nM. Inset: The same eboC37 dilutions flowed over an eboIZN39IQ(D3) surface. No binding is observed.
Figure 11:
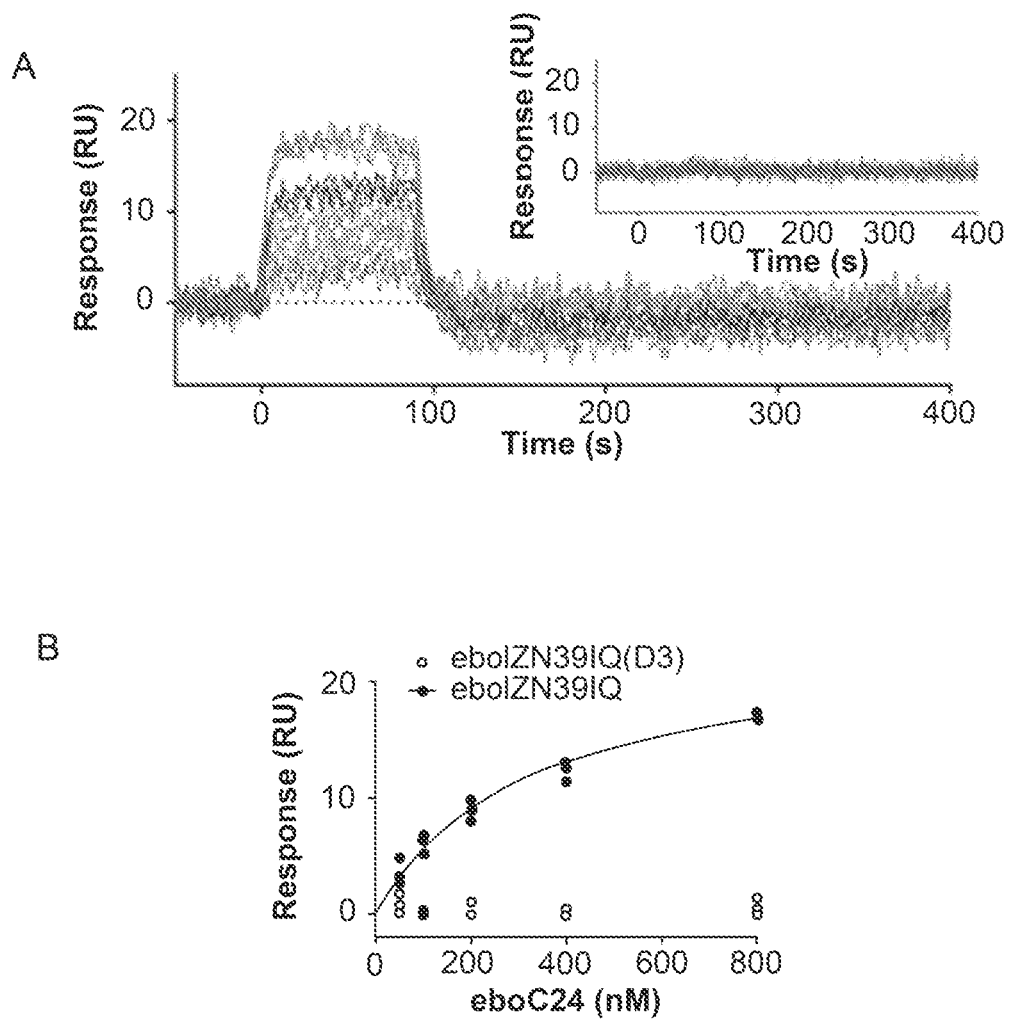
FIG. 11: Binding of the *Ebola* C-peptide to the N-trimer mimic. Sensorgram of eboC24 flowed over eboIZN39IQ in a triplicate 2-fold dilution series starting at 800 nM (ProteOn XPR36, Bio-Rad), plotted with 2nd order 2-neighbor-smoothing with a Savitzky-Golay filter (Prism 6, GraphPad Software). Each dilution is shown as a distinct color. Equilibrium response data were averaged over one minute and fitted using non-linear least-squares analysis with Prism 6.04 (GraphPad Software, Inc.). The fit indicates a $K_D$ of 310 nM. Inset: The same eboC24 dilutions flowed over an eboIZN39IQ(D3) surface. No binding is observed.

To validate that eboIZN39IQ presents the native conformation of the N-trimer found in the prehairpin intermediate, binding to its native ligand, the ebolavirus C-peptide, was characterized (FIG. 2), which binds along the entire groove of the N-trimer in the post-fusion trimer-of-hairpins conformation. Surface plasmon resonance (SPR) analysis (ProteOn XPR36, Bio-Rad) of the interaction of eboC37 with eboIZN39IQ showed a dissociation constant of 14 nM (FIG. 4), with no binding to the D3 negative control. This tight binding affinity is of the same magnitude as the HIV-1 N-trimer/C-peptide interaction(28) and indicate that eboIZN39IQ presents a native N-trimer. A shortened C-peptide (eboC24), missing the 13 N-terminal residues of eboC37, bound to eboIZN39IQ with a dissociation constant of ~300 nM and did not bind to the D3 negative control (FIG. 11).

Example 3: Crystal Structure of eboIZN21

Figure 5:
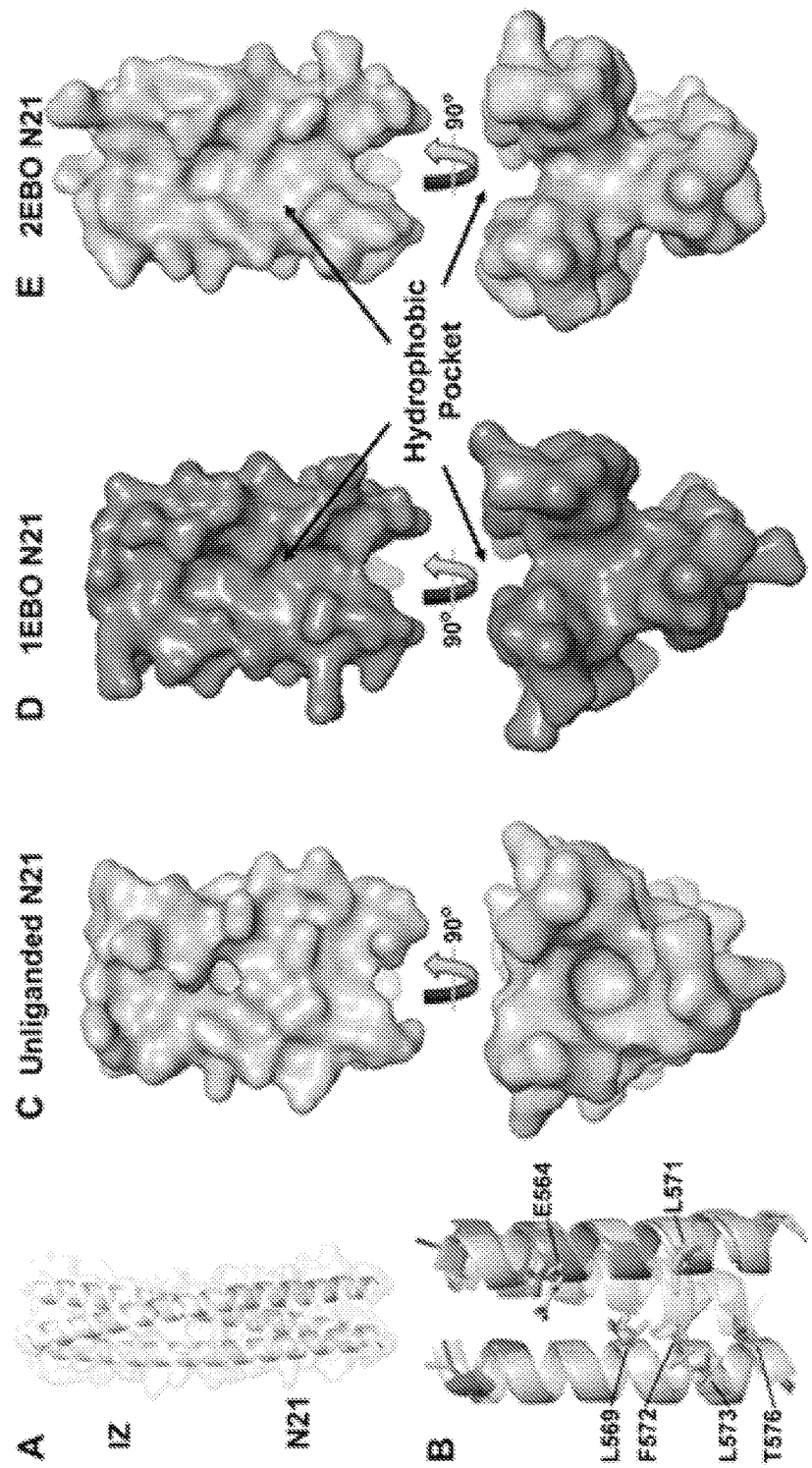
FIGS. 5A-E: Crystal structure of eboIZN21. (A) Cartoon rendering with a semi-transparent surface of the unliganded eboIZN21 structure. The IZ trimerization domain (white) and N21 region (pink) are indicated. The N21 region is shown in isolation in panels B-E. (B) Overlay of the N21 region of the unliganded structure with the N21 region of the two previously solved *Ebola* GP2 core structures containing C-peptide (PDB IDs: 1EBO and 2EBO shown as blue and green, respectively, and this color scheme is maintained in panels (C)-(E). Residues that line the N21 groove and have significantly different rotamer conformations in the unliganded structure are shown as sticks and labeled. These residues occupy some of the equivalent space occupied by C-peptide (not shown) in the liganded structures resulting in a less prominent hydrophobic pocket when viewed (in subsequent panels) as a surface. (C) Surface representation of the unliganded N21 region. The bottom panel is the view of N21 from the bottom along its 3-fold axis and is rotated approximately 90° compared to the top panel. (D)-(E) Similar views to (C) of the N21 region from the structures containing C-peptide. The prominent hydrophobic pocket in the 1EBO and 2EBO structures appears to be induced by ligand binding since the pocket is nearly absent in the unliganded structure.

The X-ray crystal structure of eboIZN21 was determined. eboIZN21 crystallized as a symmetrical trimer in space-group P 3 2 1, with one monomer in the asymmetric unit. The structure reveals eboIZN21 to be a continuous trimeric coiled coil, as designed (FIG. 5A). Crystals grew in the absence of ligand, allowing comparisons between our structure and the two previous structures of the *Ebola* 6-helix bundle (PDB IDs: 1Ebo(26) and 2Ebo(27)). Overall, there was good agreement between the N21 residues in our unliganded structure, and the previous structures with bound C-peptide as indicated by a root mean square deviation (r.m.s.d.) of 1.156 Å (1Ebo) and 1.386 Å (2Ebo) when aligned on Cα residues (FIG. 5B). However, surface renderings show that in the 6-helix bundle structures, a hydrophobic pocket is observed in the N21 region that is collapsed in the eboIZN21 structure (FIGS. 5C-5E).

Figure 12:
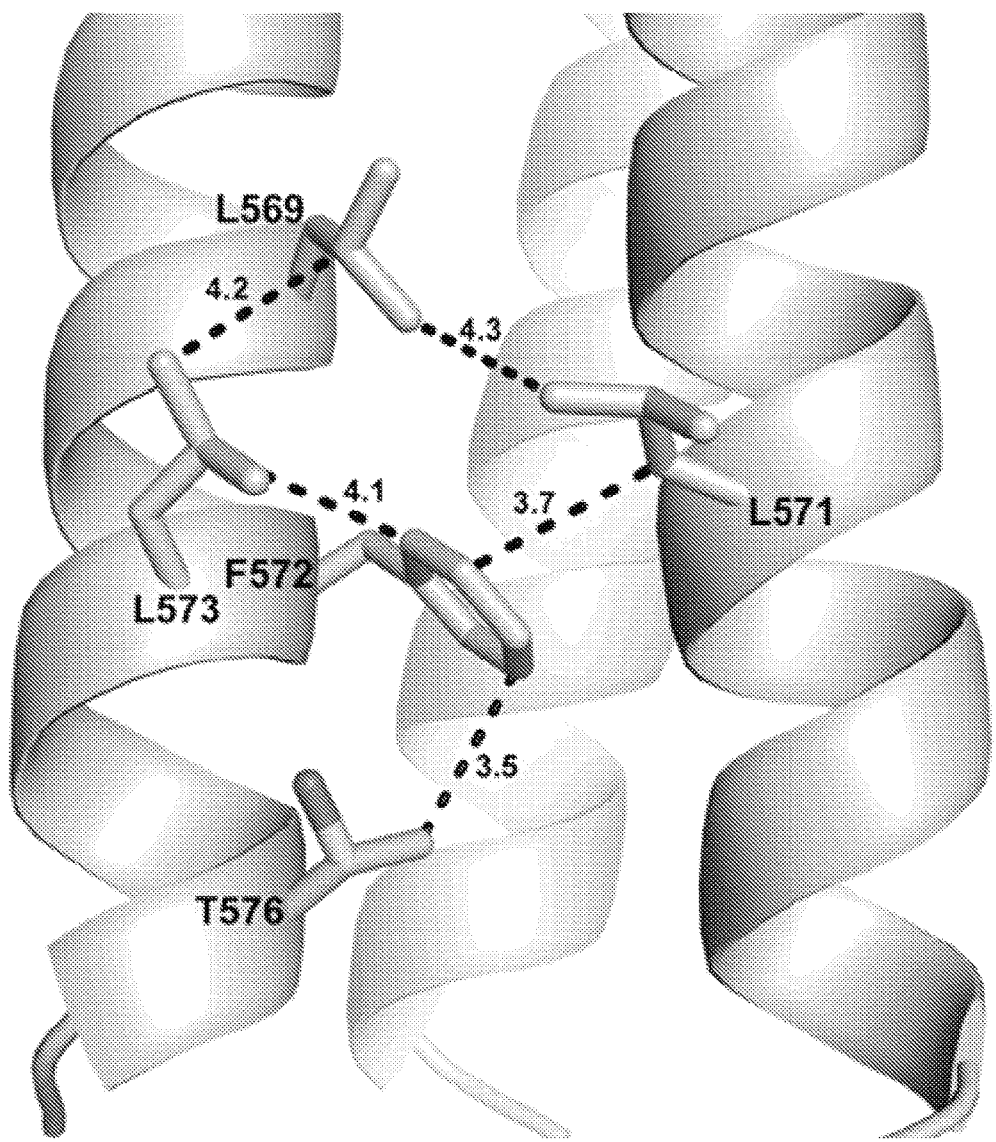
FIG. 12: Hydrophobic interactions between N21 residues in the unliganded eboIZN21 structure. A similar view to that in FIG. 5B is shown. Residues L569, L571, F572, L573, and T576 adopt alternate conformations compared to the structures containing C-peptide and form hydrophobic interactions among themselves in the absence of ligand.
Figure 13:
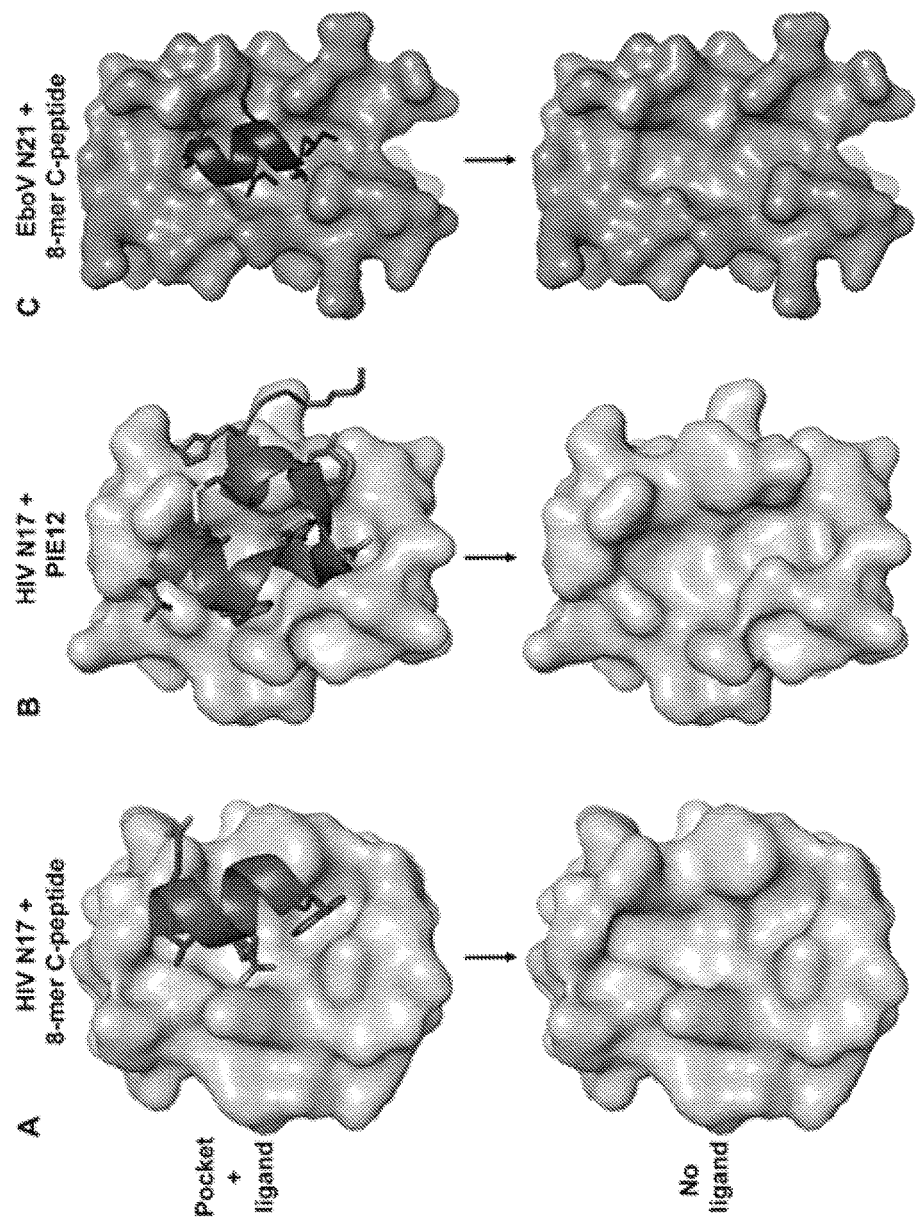
FIGS. 13A-C: Comparison of hydrophobic pockets in *Ebola* and HIV. (A) Surface representation of the N17 region comprising a hydrophobic pocket in the HIV gp41 N-trimer (orange) including a cartoon representation of the eight residues (8-mer, red) of the HIV C-peptide that interact with the pocket. C-peptide residues that specifically contact pocket-forming residues are shown as sticks. The bottom panel is the same view as the top panel but without ligand. (B) A similar view of the HIV gp41 pocket but with the D-peptide ligand, PIE12 (dark red), bound. A comparison of the C-peptide-bound and PIE12-bound pockets indicates the shape of the pocket is ligand inducible. (C) A similar view of the *Ebola* N21 region (blue) from the 1EBO crystal structure showing the *Ebola* hydrophobic pocket in the presence and absence of the 8-mer region of the *Ebola* C-peptide (dark blue) that interacts with the pocket.

The collapse of this pocket in the unliganded structure results from the side-chain conformations of several residues that fill the pocket. Specifically, in the absence of C-peptide, L569, L571, F572, L573, and T576 adopt alternate rotamers to pack together via hydrophobic interactions, and thus alter the surface contours of the ligand binding pocket (FIG. 12). The side chain of E564 is also in an alternate conformation occupying a distinct portion of the pocket (toward the top of the pocket in FIG. 5). Therefore, as seen with the analogous hydrophobic ligand-binding pocket in the HIV gp41 N-trimer (comparing structures in (29; 30; 28; 31), e.g., FIG. 13), our eboIZN21 unliganded structure suggests that the *ebolavirus* GP N21 pocket is induced by ligand binding and can likely adopt various conformations depending on the specific ligand.

The MONSTER protein interaction server (32) was used to calculate the solvent accessible surface area (SASA) buried at the interface of the *Ebola* and HIV hydrophobic pockets and the C-peptide residues that interact with them. The crystal structures of the *Ebola*(26; 27) and HIV(29; 30) 6-helix bundles reveal that in each case the pocket interacts with 8 C-peptide residues (ITDKIDQI (SEQ ID NO: 1) for *Ebola* and WMEWDREI (SEQ ID NO: 2) for HIV) (FIGS. 13A & 13C). The buried SASA at the N21 pocket/8-mer C-peptide interface is similar in the 1Ebo and 2Ebo structures at 393/348 Å$^2$ and 387/325 Å$^2$, respectively. These values are comparable to SASA buried at the HIV gp41 pocket/8-mer C-peptide interface (349/310 Å$^2$). Finally, a similar analysis between the HIV pocket and our D-peptide entry inhibitor, PIE12 (FIG. 13B), revealed that 416/391 Å$^2$ of SASA is buried at that interface(31).

Example 4: Phage Display Target Validation

To validate the *ebolavirus* N-trimer mimics as discovery targets in the context of phage display, phage clones expressing the native binding partners eboC37 and eboC24 were produced and assayed for their ability to bind to the N-trimer mimics described herein in phage clone binding assays. These experiments were designed not only to verify ligand binding but to define the best conditions for future phage display discovery efforts.

Phage display selections can be conducted in two formats: solid- and solution-phase. In solid-phase selections, the target is bound to a solid support (here, biotinylated *ebolavirus* N-trimer mimic is attached to streptavidin-coated magnetic beads), and then the phage are incubated with the immobilized target. Since common phage display libraries are multivalent (multiple copies of the library molecule are expressed on the surface of the phage, due to fusion to multi-copy coat proteins), avidity effects improve the apparent binding constant of the library clones. This avidity-induced affinity boost is beneficial when screening naïve phage libraries, where initial binders typically have low target affinities. In solution-phase, where both target and phage are incubated in solution, avidity effects are reduced. Following incubation, the bound complexes are captured through a brief interaction with a solid support (again, in this case, through a biotinylated target and streptavidin beads). At equivalent target concentrations, solution-phase selection is more stringent than solid-phase selection. The higher stringency of solution-phase is useful when screening second generation libraries for affinity maturation (i.e., peptide binding consensus libraries or antibody variable loop mutagenesis libraries) where tight binders must be distinguished from a background of moderate binders.

Figure 6:
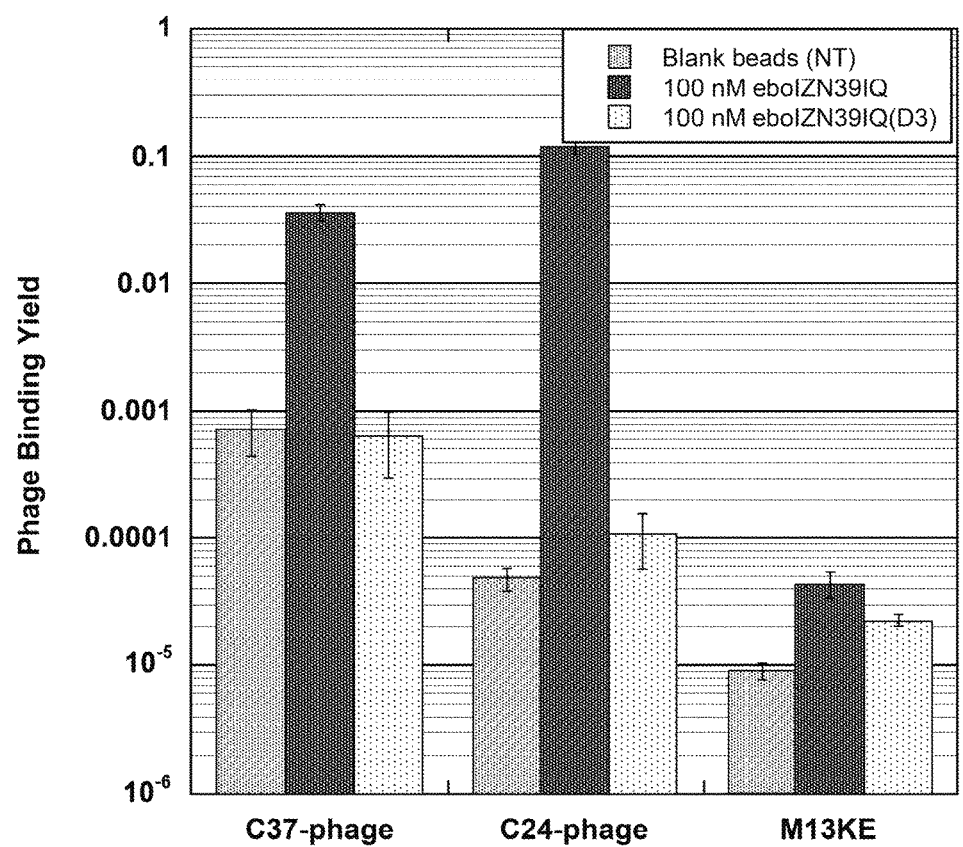
FIG. 6: Validation of eboIZN39IQ as a phage display target. Clonal phage expressing *ebolavirus* C-peptides (eboC37 or eboC24) were incubated with biotinylated eboIZN39IQ in solution followed by capture via magnetic streptavidin beads. Negative target controls include the binding site mutant, eboIZN39IQ(D3), and magnetic beads with no target (NT). Binding of M13KE (phage with no peptide clone) to all targets was also assayed. The fraction of phage bound is reported. Error bars represent standard error across triplicate experiments.

In solution-phase clonal phage binding assays carried out at pH 5.8 to mimic the endosomal environment and with biotinylated eboIZN39IQ as the target, both eboC37 and eboC24 clonal phage bound to target significantly over background (both empty beads as well as beads with our negative control, eboIZN39IQ(D3)) (FIG. 6). Also, binding of M13KE empty phage to eboIZN39IQ and eboIZN39IQ (D3) was minimal. Importantly, these data validated eboIZN39IQ as a phage display target. In addition, these data validated eboIZN39IQ(D3) as a negative control, as its clonal C-peptide phage binding is comparable to that of blank beads. In this format both C-peptide clones bound at similar levels to eboIZN39IQ, although eboC37 had greater background binding to both negative controls.

Figure 7:
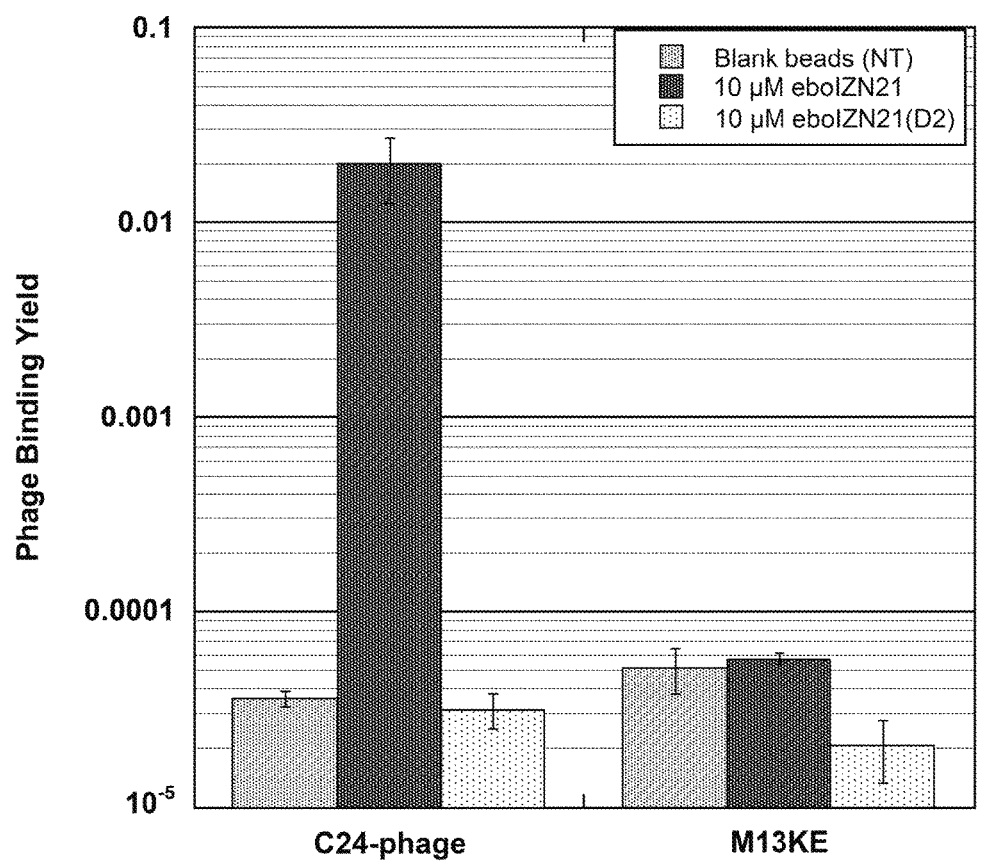
FIG. 7: Validation of eboIZN21 as a phage display target. Clonal phage expressing an *ebolavirus* C-peptide (eboC24) were incubated with biotinylated eboIZN21 bound to streptavidin magnetic beads (solid-phase conditions). Negative target controls include the binding site mutant, eboIZN21(D2), and magnetic beads with no target (NT). Binding of M13KE (phage with no peptide clone) to all targets was also assayed. The fraction of phage bound is reported. Error bars represent standard error for triplicate experiments.

Using eboIZN21 as a target in a solid-phase eboC24 clonal phage binding assay, specific binding (over two orders of magnitude over background) was seen, validating eboIZN21 as a phage display target. With the low level of eboC24 phage binding to eboIZN21(D2) (similar to eboC24 binding to blank beads), the binding site mutant was also verified as a negative control. In addition, only a very low level of M13KE empty phage binding to eboIZN21 and eboIZN21(D2) was observed (FIG. 7).

Figure 8:
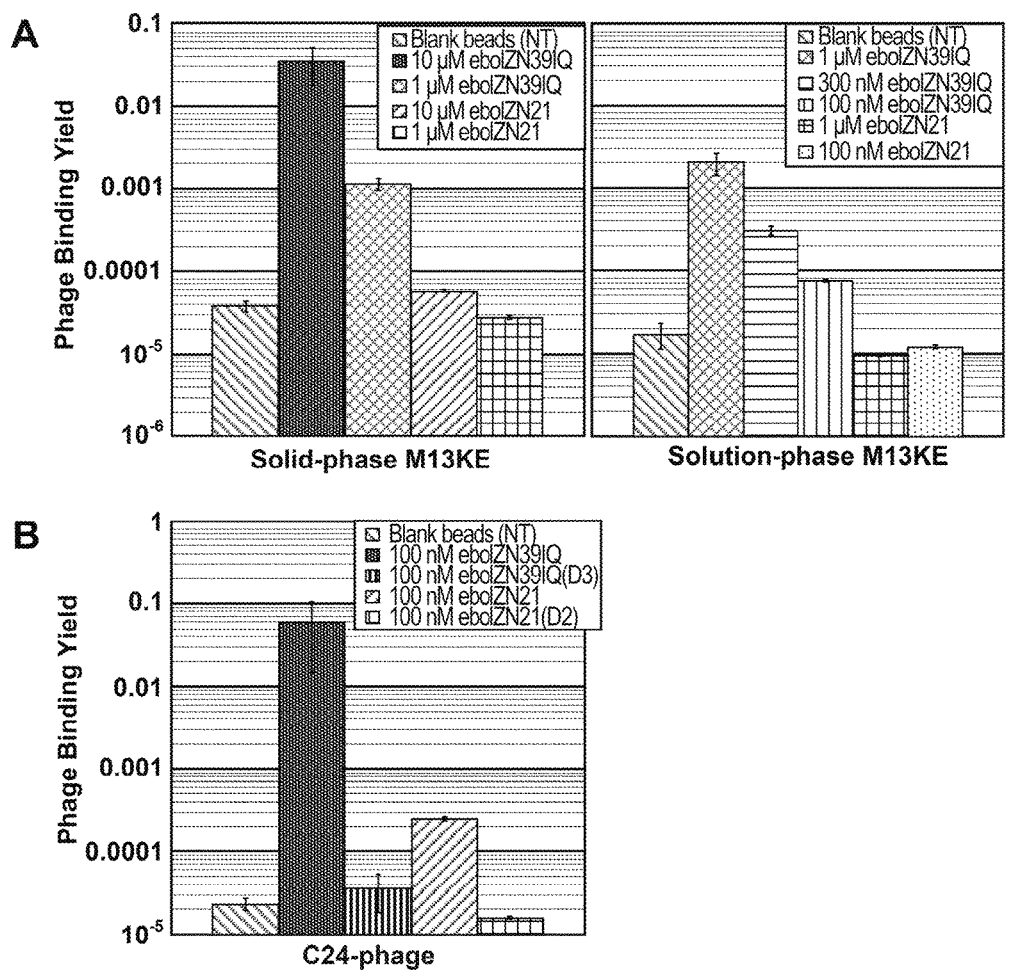
FIGS. 8A-B: Comparing the two *ebolavirus* N-trimer mimics as phage display targets. (A) Phage background binding is greater to eboIZN39IQ than to eboIZN21. Phage binding assay showing M13KE control phage binding to biotinylated eboIZN39IQ and eboIZN21 under both solid-phase (left) and solution-phase (right) conditions. Magnetic beads with no target (NT) were used as a negative control. The fraction of phage bound is reported. Error bars represent standard deviation for duplicate experiments (solid-phase) and standard error for four or more replicates (solution-phase). (B) High stringency solution-phase binding shows an affinity difference for the specific binding of eboC24 to the two N-trimer mimics. Clonal phage expressing eboC24 were incubated with biotinylated N-trimer in solution followed by capture via magnetic streptavidin beads. Negative target controls include the binding site mutants and magnetic beads with no target (NT). For NT, error bars represent standard error across triplicate experiments. The remaining error bars represent standard deviation for duplicate experiments.

Low phage background binding to targets is required in order to discern specific binding during phage panning rounds. To compare this feature for our N-trimer mimics, we analyzed empty M13KE phage binding to both targets under varying conditions (FIG. 8). In both solid- and solution-phase formats, M13KE phage showed significantly higher binding to eboIZN39IQ beads than to blank beads, although the difference was reduced for solution phase. For the eboIZN21 target, phage background binding was drastically reduced in comparison to eboIZN39IQ, and binding of M13KE phage was similar to both target and blank beads in solid and solution phase. Under very stringent conditions (solution phase, 100 nM target), the M13KE background binding to eboIZN39IQ was minimized, and a large affinity difference for eboC24 binding to eboIZN39IQ vs. eboIZN21 could be seen. This affinity difference is likely biologically relevant, as the trimer-of-hairpins structures(26; 27) show that the binding site of eboC24 extends past the C-terminus of N21.

The first step of a phage display discovery process is to screen a naïve phage display library for binding to the desired target. In such a first selection, where the library diversity only partially samples the large potential sequence space (for example, a naïve peptide 12-mer library has >$10^{15}$ possible sequences (20"), whereas the typical diversity of a phage display library is <$10^{10}$), the best binders identified are modest, typically with low to mid micromolar affinities. Therefore, the selection pressure during phage panning may also be modest. Standard naïve phage display starting conditions are 10 µM target presented on solid-phase (i.e., 30 µL of 10 µM target immobilized onto magnetic beads) (23). As illustrated in FIG. 8, M13KE binding to eboIZN39IQ was nearly saturated at this condition, and therefore it would not be possible to identify binding over background. 10% phage binding is considered saturating, as binding yields of even strong binders do not generally exceed this level (likely due to proteolysis of displayed peptides). Under the same conditions, the eboIZN21 background binding was >600-fold lower and similar to blank bead binding, ideal starting conditions for naïve phage display. Therefore, eboIZN21 was a target for phage display discovery efforts. Additionally, the eboC24-phage can serve as an important positive control to use during naïve phage display to validate the conditions used to capture weak, but specific binders. Notably, in addition to having ideal behavior in phage display, the N21 region is also identical across all *ebolavirus* species and highly conserved among filoviruses (95% conserved) (FIG. 2A). eboIZN39IQ provides a useful target for higher stringency solution-phase phage display and could be used to screen secondary libraries for affinity optimization of ligands identified from the naïve library. This could be especially useful for extending the binding interface of the ligands further along the N-trimer groove.

Example 5: Mirror-Image Phage Display

Mirror-image phage display is an adaptation of standard peptide phage display and is used to identify D-peptides that bind to a target of interest(35; 23). D-peptides are composed of D-amino acids and are the mirror-image of naturally occurring L-peptides. D-peptides have several important potential advantages as drug candidates (as reviewed (36)). As peptides, they may be capable of preventing large protein/protein interactions, something that is generally not possible for small molecules. This gives them the potential of being highly potent (strong clinical efficacy) and specific (low toxicity). In addition, since they tend to be resistant to protease degradation(37), D-peptides should enjoy a long in vivo half-life and reduced immunogenicity(3 8).

Figure 14:
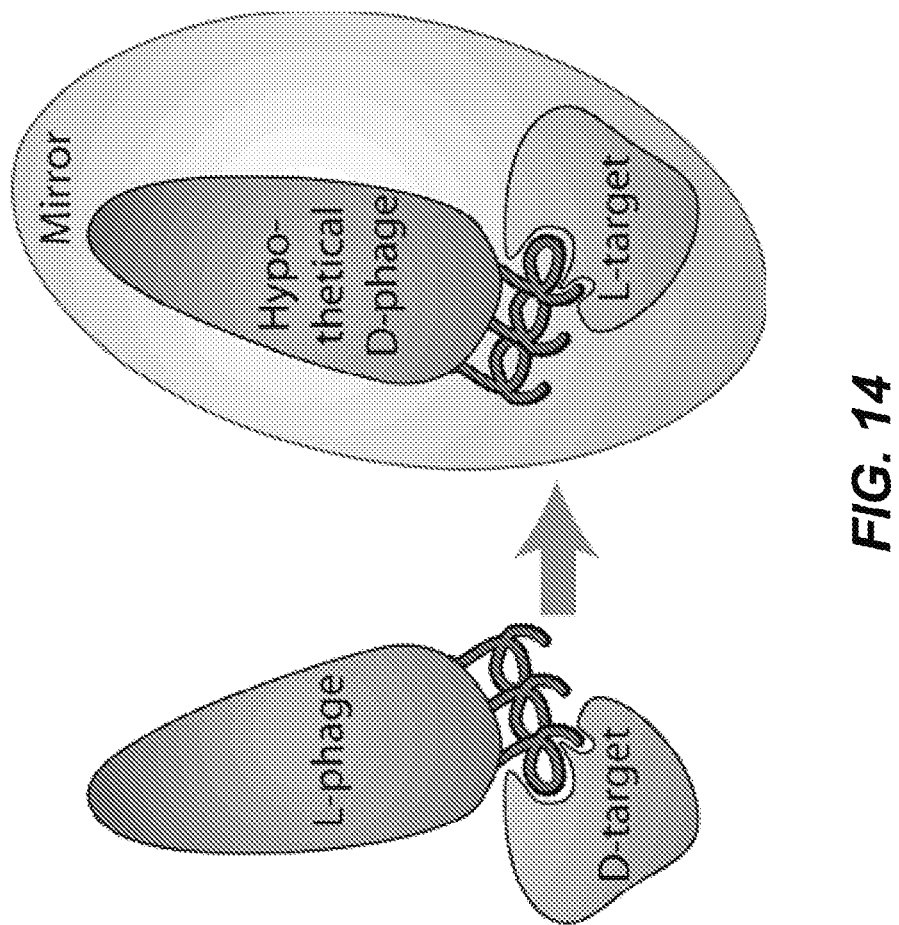
FIG. 14: Mirror Image Phage Display. In mirror-image phage display, the peptide/protein target is synthesized with D-amino acids (D-target) and forms the mirror-image of the natural L-target. Phage expressing a library of natural L-peptides (L-phage) are screened for binding to the D-target. The peptides from the specific phage clone binders are then synthesized with D-amino acids (mimicking a D-phage), and by the law of symmetry, the D-peptides will bind the natural L-target.

D-peptides are attractive as *ebolavirus* entry inhibitors, as their resistance to endosomal proteases would be highly advantageous. In traditional peptide phage display, a library of phage, each with a unique peptide displayed on its surface, is screened against a target(39). The phage links phenotype (target binding) to genotype (the DNA encoding the surface peptide is in the genome). In mirror-image phage display, the screening target is chemically synthesized from D-amino acids and therefore forms the mirror-image structure of the natural L-target (FIG. 14). Phage display using the D-target is performed, and identified L-peptides that bind the D-target are then chemically synthesized with D-amino acids. By the law of symmetry, these D-peptides bind the natural L-target. Therefore, unlike with traditional phage display, mirror-image phage display targets are limited in size to those that can be chemically synthesized.

Figure 15A:
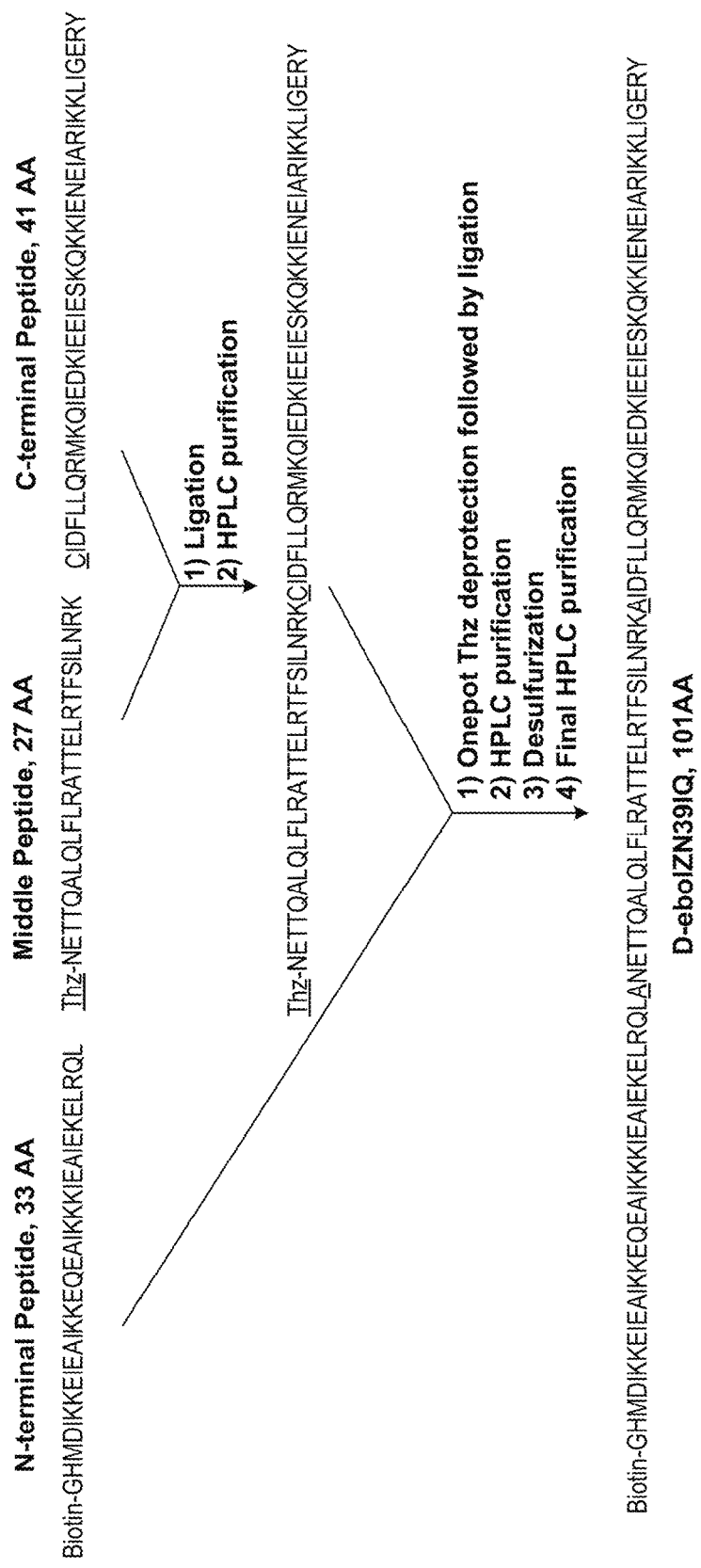
Figures 15B, 15C:
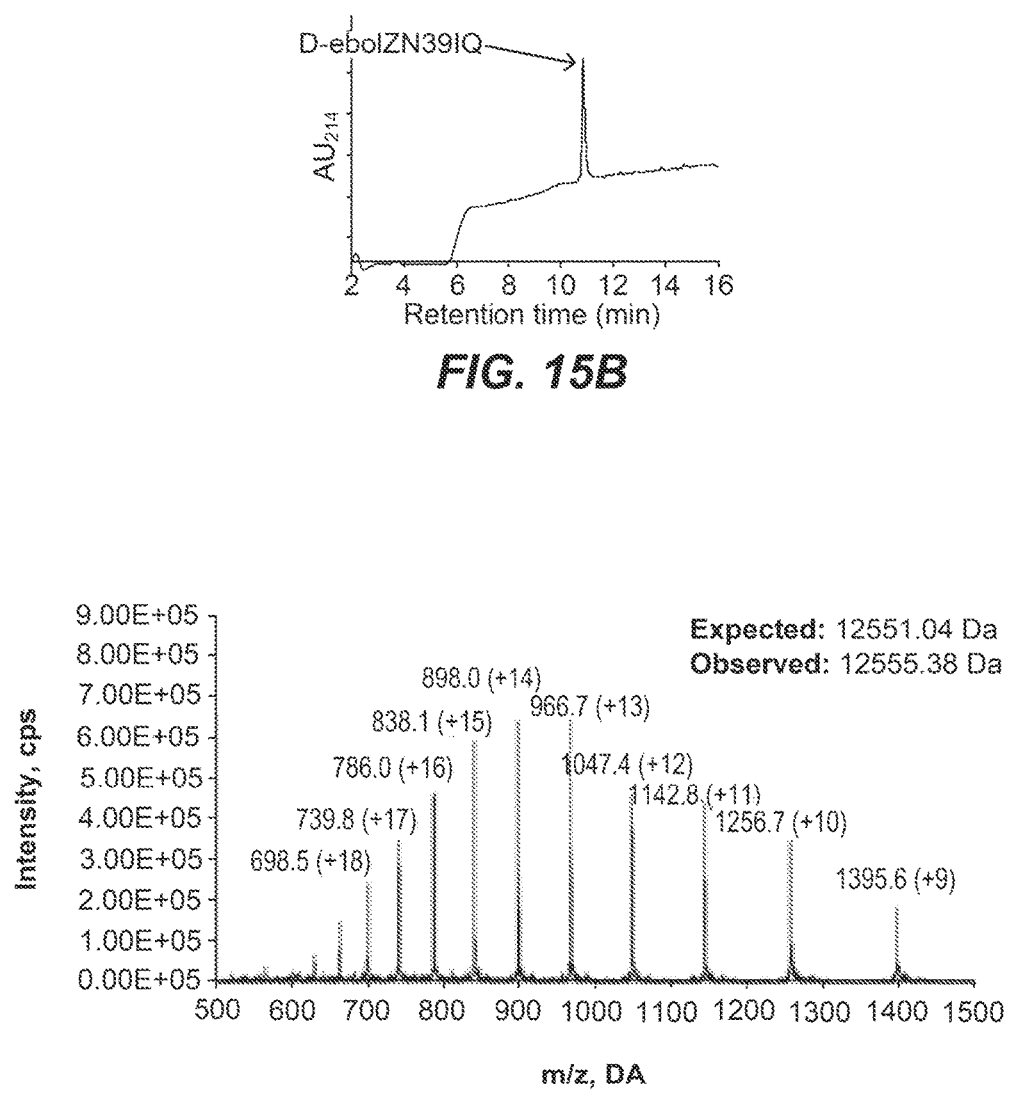

In order to prepare *ebolavirus* N-trimers described herein as mirror-image phage display targets, they were synthesized as D-peptides. At a length of 48 amino acids, D-eboIZN21 and D-eboIZN21(D2) were readily synthesized through standard solid-phase peptide synthesis (SPPS) techniques. Importantly, even though the 101-residue length of eboIZN39IQ is beyond the scope of standard SPPS, modern chemoselective ligation techniques(40) allowed for its assembly from multiple peptide segments. D-eboIZN39IQ, was assembled using native chemical ligation(41) and metal-free desulfurization(42), in which cysteine residues are introduced at native alanine sites to facilitate ligation and then converted back to alanine through desulfurization (FIG. 15A). D-eboIZN39IQ (SEQ ID NO:29) was assembled from three synthetic segments of relatively equal length (27-41 residues): N-terminal peptide (33 residues; SEQ ID NO: 25); middle peptide (27 residues; SEQ ID NO:26; and C-terminal peptide (41 residues; SEQ ID NO:27). SEQ ID NO:28 represents the ligation product of the middle peptide (SEQ ID NO:26) and C-terminal peptide (SEQ ID NO:27), which was then ligated to the N-terminal peptide (SEQ ID NO:25) (see, also Materials and Methods section). The production of D-eboIZN39IQ(D3) required a novel assembly strategy, as one of the alanines (used in D-eboIZN39IQ as a ligation junction) is mutated to aspartate. Therefore, D-eboIZN39IQ (D3) was assembled from two synthetic segments of lengths 33 and 68 amino acids. The final peptide products were confirmed by LC/MS (FIGS. 15B & 15C).

Figure 16:
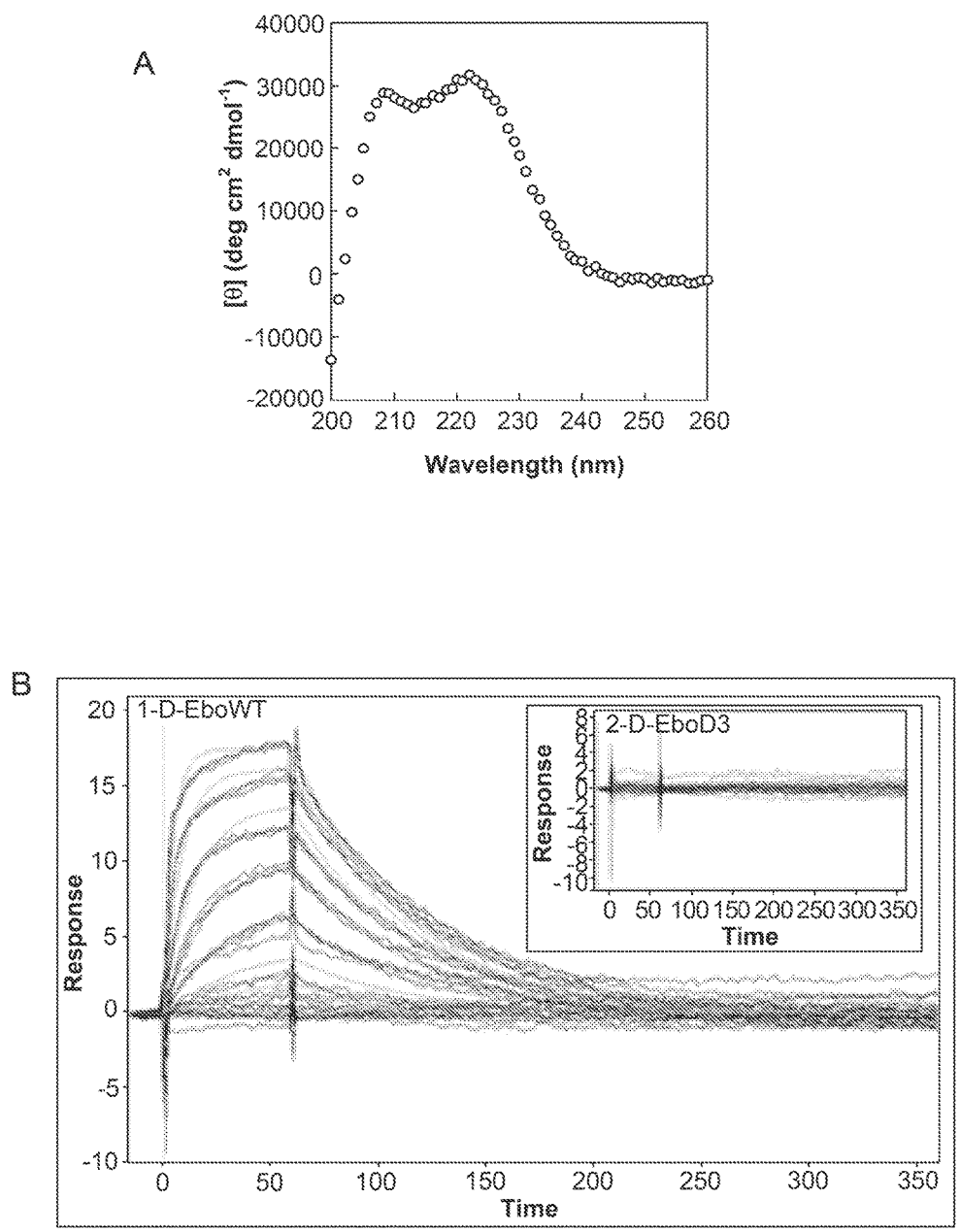
FIGS. 16A-B: Biophysical characterization of the D-versions of the Ebola N-trimer mimics. (A) CD spectrum of 10 µM D-eboIZN21 at 4° C. in 50 mM sodium phosphate pH 5.8, 150 mM NaCl which is indicative of a highly helical conformation. The positive values are as expected for this mirror-image helix. (B) Analysis of binding of D-eboC37 to D-eboIZN39IQ via SPR (Biacore 3000). D-eboC37 was flowed over D-eboIZN39IQ (and D-eboIZN39IQ(D3); inset) in a 7-member 2-fold dilution series starting at 60 nM in duplicate. The fit indicates a $K_D$ of 5.8 nM. No binding is observed to D-eboIZN39IQ(D3). SPR methods: SPR analysis was conducted on a CMS sensor chip (GE Healthcare) loaded with 10,000 RU streptavidin followed by capturing ~400 RU biotin-D-eboIZN39IQ (at 40 nM in PBST* running buffer). Using Kinject, a 2-fold dilution series of D-eboC37 was flowed over the chip in duplicate at RT starting at 60 nM. A five minute dissociation time was used to ensure the response fully recovered to baseline prior to the next injection.

CD analysis of D-eboIZN21 confirms it possesses a mirror-image helical structure (FIG. 16A). SPR analysis of D-eboC37 binding to D-eboIZN39IQ showed a similar binding affinity to the L-peptide interaction and validated the functionality of D-eboIZN39IQ (FIG. 16B). Preliminary phage display experiments with these D-targets demonstrated the same M13KE binding properties as the L-versions (data not shown), verifying the strategy of screening naïve libraries with the D-eboIZN21 target, and employing D-eboIZN39IQ for subsequent affinity optimization efforts.

Example 6: Vulnerability of the *Ebolavirus* Prehairpin Intermediate to a High Potency Inhibitor A prerequisite for the success of drug discovery efforts targeting the *ebolavirus* N-trimer mimics is the exposure of a vulnerable prehairpin intermediate during viral entry. For *ebolavirus*, an early report showed C-peptide inhibition activity at mM concentrations(46), and more recent reports described improved inhibitory activity (mid µM) of C-peptides with an endosomal localization tag(47; 48). The *ebolavirus* N-trimer, eboIZN39IQ, provides an additional tool with which to explore the vulnerability of the prehairpin intermediate.

eboIZN39IQ inhibited entry in our pseudovirus system in which *ebolavirus* GP (representative species, *Zaire*) was expressed on the surface of an HIV particle (FIG. 9A), with an average $IC_{50}$ of 320 nM. The anti-*ebolavirus* activity of our negative control, eboIZN39IQ(D3), was ~30-fold diminished, with an $IC_{50}$ of 11 µM. It is difficult to determine the exact nature of the modest eboIZN39IQ(D3) activity, as it is not seen against a vesicular stomatitis virus glycoprotein pseudotype (VSV), and no morphological changes (indicative of toxicity) were observed. It is possible the modest eboIZN39IQ(D3) activity could be due to residual prehairpin intermediate binding activity. eboIZN39IQ demonstrated modest activity against *marburgvirus* (another member of the filovirus family), at an $IC_{50}$ of 5.7 μM. This was ~2-fold better than the eboIZN39IQ(D3) anti-*marburgvirus* activity.

The ability of eboIZN39IQ to inhibit the entry of wild-type *ebolavirus* and *marburgvirus* was also assessed using a filovirus immunofluorescence assay under BSL4 conditions (FIG. 9B). eboIZN39IQ was significantly less potent in this assay, but there was still 67% inhibition of entry at the highest concentration tested, 10 μM, and no inhibition by our negative D3 control. Also, no activity was seen against *marburgvirus*. Taken together, these data validated the presence of a vulnerable prehairpin intermediate during the *ebolavirus* entry process.

Unlike HIV-1, *ebolavirus* enters cells via endocytosis and initiates membrane fusion late in the endosomal pathway. Therefore, *ebolavirus* entry inhibitors may have to enter into and be active in endosomes. Although eboIZN39IQ does not possess a specific tag to localize it to endosomes, it is highly charged on its surface (with both positive and negatively charged side chains), and the inhibitory activity we observed in both the pseudovirus and authentic *ebolavirus* systems was dependent on the presence of the standard viral assay additive DEAE-dextran. Without being bound by a particular theory, it seems possible that, especially in the presence of the cationic DEAE-dextran that would reduce electrostatic repulsion between the negative charges of eboIZN39IQ and the membrane, the highly charged N-trimer mimic would naturally interact with the anionic cell membrane, allowing it to access the endosome more efficiently than C-peptides.

In addition to serving as drug targets, the *ebolavirus* N-trimer mimics described herein may also be useful as cell biological tools. For example, fluorescently labeled N-trimers may be used in cell culture experiments to track the appearance of the prehairpin intermediate during the viral entry event.

Materials and Methods (i) Reagents

Plasmids and cells were obtained from the indicated sources: pKA8 vector (gift from C. Hill), pEBB-HXB2 (gift from B. Chen(51)), SV-ZeboGPAmuc and SVMarVGP (gift from M. Farzan)(52), BLR(DE3)pLysS *E. coli* (EMD Millipore, Billerica, Mass.), BL21-Gold(DE3)pLysS *E. coli* and XL-1 Blue *E. coli* (Agilent Technologies, Santa Clara, Calif.). pNL4-3.Luc.R-E- (N. Landau)(53; 54) and HOS-CD4-fusin (N.Landau)(55; 56) were obtained from the NIH AIDS Research and Reference Program. The mammalian cells were propagated in standard tissue culture medium, Dulbecco's Modified Eagle Medium (DMEM) supplemented with 10% fetal calf serum and L-glu (Life Technologies, Grand Island, N.Y.).

(ii) Recombinant Peptide Production and Purification

The DNA encoding eboIZN39IQ and eboIZN39IQ(D3) was produced via PCR gene synthesis. The $IZ_m$ and IQ fragments were PCR amplified from plasmids encoding HIV-1 N-trimer mimics (e.g., (57)). An NdeI site was included in the 5' PCR primer for $IZ_m$, and a BamHI site was included in the 3' PCR primer for IQ. The *ebolavirus* N39 sequence from the species *Zaire ebolavirus* (58) was synthesized in two overlapping oligos with optimized codons and companion primers. All internal primers contained complementary sequences so the three separate components, $IZ_m$, N39 and IQ could be annealed and amplified together. The resulting DNA fragment was cloned into the NdeI/BamHI cloning sites of pKA8, validated by sequencing and expressed in BLR(DE3)pLysS cells using an autoinduction protocol. Specifically, cultures were inoculated from a single colony and grown overnight at 37° C. in autoinduction media(59). The resultant peptide has an N-terminal His tag ($His_8$) followed by a TEV cleavage site (ENLYFQG) (SEQ ID NO: 3). A single tyrosine was placed at the end of the sequence to facilitate concentration determination via absorbance at 280 nm. The peptides were resuspended from inclusion bodies using a Ni++ Binding Buffer (20 nM sodium phosphate pH 8.0, 300 mM NaCl, 10 mM imidazole)+6 M GuHCl, and purified via gravity flow Ni++ affinity chromatography (HIS-Select Nickel Affinity Gel, Sigma Aldrich, St. Louis, Mo.). The purified peptide was dialyzed into 5% acetic acid and further purified by reverse phase HPLC on a C18 column (Vydac, Grace, Columbia, Md.) and lyophilized. Peptide powder was resuspended in water and diluted to 0.2 mg/mL in 50 mM sodium phosphate pH 6.5, 0.5 mM EDTA, 1 mM DTT and digested with a solubility-enhanced tobacco etch virus NIa protease (TEVse, gift of C. Hill, based on published modifications(60; 61)) overnight at 30° C. The digested peptide was dialyzed into 5% acetic acid and then HPLC purified and lyophilized. The final peptide sequences are: GHMDIKKEIEAIK-KEQEAIKKKIEAIEKELRQLANETTQ(A/D)LQLFLR(A/D)TTE LRTFSILNRK(A/D)IDFLLQRMKQIEDKIEE-IESKQKKIENEIARIKKLIGERY (SEQ ID NO: 4), with $IZ_m$ and IQ shown in bold, respectively, the *ebolavirus* N-trimer in italics, and the three alanine positions that are changed to aspartate in the D3 mutant in parentheses.

Biotinylated eboIZN39IQ and eboIZN39IQ(D3) for SPR analysis and phage display were expressed from plasmids that are modified from those described above. Using PCR, a CGG sequence was added N-terminal to IZ (GHMCG-GDIKK . . . )(SEQ ID NO: 5). Expression and purification were as described above with additional reduction steps included to keep the cysteine reduced during purification (100 mM DTT treatment after Ni++ affinity chromatography and 50 mM TCEP treatment after TEV digestion). The purified protein was biotinylated with EZ-link Maleimide-PEG2-biotin (Thermo Scientific, Waltham, Mass.). The purified lyophilized powder was resuspended at 1 mM in freshly prepared reaction buffer (6 M GuHCl, 150 mM NaCl, 100 mM $Na_2HPO_4$, 5 mM TCEP) and the biotinylation reagent was added at 5 mM and allowed to react for 4 hr at RT. The biotinylated peptides were purified by reverse phase HPLC on a C18 column (Waters) and lyophilized. The mass of the peptide was confirmed by LC/MS (AB Sciex API 3000 LC/MS/MS system, Framingham, Mass.).

(iii) Peptide Synthesis eboIZN21, eboIZN21(D2), eboC37 and eboC24 were chemically synthesized using solid-phase peptide synthesis (SPPS) with Fmoc-amino acids (CBL Biopharma, Boulder, Colo.) on the Prelude peptide synthesizer (Protein Technologies, Inc (PTI), Tucson, Ariz.). A single tyrosine was placed at the N-terminus of both eboIZN21 and eboIZN21(D2) to facilitate concentration determination via absorbance at 280 nm. The peptides were synthesized on TentaGel R RAM resin (Rapp Polymere, Germany) to yield C-terminal amide-capped peptides. Standard synthesis scales were 25-32 μmol per peptide. Standard amino acid coupling was as follows: 3×3 min deprotection with 20% piperidine in DMF followed by 25 min couplings with 72.2 mM amino acid (200 mM stocks in NMP), 71.5 mM HATU (200 mM stock in DMF), and 166.7 mM NMM (600 mM stock in DMF). Biotinylation was achieved with N-Biotinyl-NH-(PEG)$_2$-COOH-DIPEA (Novabiochem, EMD Millipore) coupling for 2 hrs. N-terminal capping was accomplished in 30 min with 2 mL acetic anhydride and 2 mL 0.6 M NMM. Peptide cleavage from resin was accomplished off-line with 92.5% TFA, 2.5% EDT, 2.5% TIS, 2.5% H$_2$O when the peptide contained Met or Cys residue(s) or with 95% TFA, 2.5% TIS, 2.5% H$_2$O in the absence of any Met/Cys residues followed by precipitation/washing with diethylether. All peptides were purified by reverse-phase HPLC on a Waters (Milford, Mass.) BEH X-Bridge C18 column (10 μm, 300 Å, 19×250 mm) with a water/ACN gradient in 0.1% TFA. All peptides were lyophilized and their molecular weight verified by LC/MS.

D-eboIZN39IQ was assembled from three synthetic peptide segments via native chemical ligation/metal-free desulfurization. Peptides were synthesized via Fmoc-SPPS on a PTI PS3 peptide synthesizer at 100 μmol scale. The C-terminal peptide was synthesized on Rink Amide AM resin LL (Novabiochem) and the other two segments were synthesized on Dawson Dbz AM resin (Novabiochem). The C-terminal segment contained an N-terminal cysteine residue in the place of a native alanine for use in native chemical ligation (CIDFLLQRMKQIEDKIEEIESKQKKIENE-IARIKKLIGERY) (SEQ ID NO: 6). For the same reason, the middle segment contained an N-terminal Boc-L-thiazolidine-4-carboxylic acid (Boc-THZ-OH, Bachem, Torrance, Calif.) as its N-terminal residue in place of the native alanine at that position((THZ)-NETTQALQLFLRATTELRTFSIL-NRK) (SEQ ID NO: 7). The N-terminus of the N-terminal peptide (GHMDIKKEIEAIKKEQEAIKKKIEAIEKEL-RQL) (SEQ ID NO: 8) was biotinylated with N-Biotinyl-NH-(PEG)2-COOH DIPEA (Novabiochem). For peptides synthesized on Dawson Dbz AM resin, the C-terminal linker was converted to the resin bound benzimidazolinone (Nbz) according to manufacturer recommendations. Cleavage of all peptides was performed according to standard procedures. Peptides were purified by reverse-phase HPLC on a Waters BEH X-Bridge C18 column (10 μm, 300 Å, 19×250 mm) with a water/acetonitrile gradient in 0.1% TFA. Ligations were performed according to (62) with peptide concentrations ~2 mM. Following ligation between the C-terminal and middle segments, the N-terminal THZ residue was converted to cysteine by dissolving the purified ligation product in 6 M GuHCl, 200 mM sodium phosphate, 200 mM methoxyamine HCl, pH 4. After THZ to Cys conversion was achieved, the buffer was brought to 200 mM MPAA and 20 mM TCEP, the pH was adjusted to 7, and the N-terminal peptide was added to the solution for the final ligation. Following purification of the ligation product by reverse-phase HPLC, the cysteine residues at the ligation junctions were converted to the native alanine residues via a metal-free, radical-mediated desulfurization strategy essentially as described in (42) except tBuSH was replaced with glutathione and desulfurizations were performed at 37° C. eboIZN39IQ(D3) was synthesized in an analogous (though simplified) manner using two peptide segments.

(iv) Preparation of Peptide Samples for Biophysical Analysis

For biophysical analyses, peptide stocks were prepared in water from lyophilized peptide at concentrations of 400 μM or greater for a minimum absorbance at 280 nm of 0.1 in a 1 cm pathlength cuvette. Stocks were centrifuged at 18,000 xg for 10 min to remove aggregates. Absorbance at 280 nm (using $\varepsilon_{280}$ of 1408 M$^{-1}$cm$^{-1}$ for tyrosine) was used to determine stock concentrations(63). For eboIZN39IQ and eboIZN39IQ(D3), both recombinant and synthetic, UV absorbance consistently overestimated the concentration of the stocks (as evidenced by an unusually high 260/280 ratio as well as CD traces whose shape depicted ideal coiled coils but whose signal had a lower than expected absolute value). Therefore, the concentrations of these stocks were determined via quantitative amino acid analysis. The peptides were then diluted to the desired concentration in 50 mM sodium phosphate pH 5.8, 150 mM NaCl. For eboIZN21 and eboIZN21(D2), all experiments described in this paper were performed with biotinylated peptide. For eboIZN39IQ and eboIZN39IQ(D3), CD, AUC and viral infectivity were performed with non-biotinylated material, whereas SPR and phage display used biotinylated material.

(v) Circular Dichrosim

Circular dichrosim (CD) data were obtained using an AVIV Model 410 spectrophotometer (AVIV, Lakewood, N.J.). Samples were analyzed in a 1 mm pathlength quartz cuvette at 25, 37, and 50° C. Prior to CD analysis, prepared samples (in 50 mM sodium phosphate pH 5.8, 150 mM NaCl) were centrifuged at 18,000 Xg for 10 min to remove aggregates. CD data were scanned in triplicate and buffer subtracted. Final CD data were presented according to mean residue ellipticity equation, $[\theta]=100*\theta/[(n-1)*(l)*(c)]$, where $\theta$ is observed ellipticity, n−1 is number of peptide bonds, l is the pathlength in cm, and c is the peptide concentration in mM. Due to aggregation observed with eboIZN39IQ and eboIZN39IQ(D3) upon initial dilution in CD buffer, their final concentrations were corrected from the original amino acid analysis values based on the ratio of ellipticity at 222 nm post- and pre-centrifugation ($\theta_{222\text{-}post\text{-}spin}/\theta_{222\text{-}pre\text{-}spin}$).

(vi) Analytical Ultracentrifugation Sedimentation Equilibrium

Using an Optima XL-1 Analytical Ultracentrifuge (Beckman Coulter, Brea, Calif.), sedimentation equilibrium analysis was performed on each peptide at three concentrations each (a starting concentration and two 2-fold dilutions, with typical starting concentrations between 10-30 μM). Dilutions were prepared in matching buffer (50 mM sodium phosphate, 150 mM NaCl, pH 5.8), and the same buffer was used for blanks Each sample was spun until equilibrium, typically ~24 hours, at a minimum of two speeds, but typically three speeds (18,000, 21,000 and 24,000 RPM). Each data set was globally fit to a floating molecular weight single ideal species with a non-linear least squares algorithm as implemented in HETEROANALYSIS(64). Fits are reported as the observed, or fit, molecular weight divided by the calculated molecular weight of a monomer ($M_{obs}/M_{calc}$). Buffer densities and protein partial specific volumes were calculated with SEDNTERP (version 1.09)(65). For the biotinylated peptides, partial specific volumes were adjusted based on reported values for PEG(66).

(vii) Surface Plasmon Resonance

SPR analysis was conducted on the Bio-Rad (Hercules, Calif.) ProteOn XPR36 instrument in PBS* running buffer (50 mM sodium phosphate, 150 mM NaCl, pH 5.8)+0.1 mg/mL BSA and 0.01% Tween-20. Approximately 600 RUs of biotin-eboIZN39IQ (in the presence of eboC37) and biotin-eboIZN39IQ(D3) targets (200 nM stocks ultracentrifuged for 30 min at 45,000 rpm) were loaded at 67 nM onto the NLC neutravidin-coated chip (Bio-Rad), followed by blocking using 450 μM biotin. Using the one-shot kinetics method, a 2-fold dilution series was performed in triplicate at RT starting at 60 nM for eboC37 and a 3-fold dilution series in triplicate at RT starting at 800 nM for eboC24. 10 min dissociation time for eboC37 and 5 min dissociation time for eboC24 were used to ensure the response fully recovered to baseline prior to the next injection. Data were corrected by subtracting blank surface and blank buffer reference injections, and the kinetics (for eboC37) and equilibrium (for eboC24) were globally fit to the Langmuir model for 1:1 binding(67) using ProteOn Manager software (Bio-Rad).

(viii) Crystallization eboIZN21 was dissolved in ddH20 to a concentration of ~10 mg/mL and centrifuged at 18,000 rcf for 10 min. Sitting-drop vapor-diffusion crystal trials were set up using a Phoenix crystallization robot (Art Robbins Instruments, Sunnyvale, Calif.). Crystals grew at 4° C. in drops containing a 2:1 ratio of peptide to well solution, which consisted of 30% (v/v) 1,2-propanediol, 100 mM HEPES pH 7.5, 20% (v/v) PEG-400. The crystals were flash frozen in liquid nitrogen without the need for additional cryoprotection and determined to be in spacegroup P321 with unit cell dimensions a=b=38.51, c=72.59. Preliminary diffraction was used to predict that the crystals contained a single eboIZN21 monomer in the asymmetric unit.

(ix) Data Collection, Structure Determination and Refinement

A native dataset was collected at the (beam line 7-1) Stanford Synchrotron Radiation Lightsource. Data were integrated and scaled to 2.15 Å using HKL2000 (68). In order to rule out the possibility of twinning, data were initially scaled in space group P3 and analyzed with the program Xtriage (71), which indicated that the data are untwinned and that the correct spacegroup is P321. A model that consisted of a canonical helix appropriate to the size and sequence of the IZ domain and the N21 region of Ebola GP (PDB ID: 1Ebo) was used for molecular replacement using the program Phaser (69). A single eboIZN21 monomer was found in the asymmetric unit; the long axis of the molecule parallel to the crystallographic 3-fold, recapitulating a 3-fold symmetric trimer. Subsequent model building, structure refinement, and validation were performed with Coot (70), PHENIX Refine (71) and MolProbity (72) software, respectively. The final model was refined to a crystallographic R-value=0.2724 and Rfree=0.2937 with good geometry (Table 2). The dataset consists of 3991 reflections to 2.15 Å resolution, so the test set (10% random selection) provides a relatively poor measure of Rfree. Additional refinements were carried out in spacegroup P3 allowing all possible twin laws, to further verify (by monitoring Rfree) that the correct spacegoup is P321 with a monomer in the asymmetric unit. A composite omit map agreed well with the final model, indicating good sidechain density throughout. Data collection and final refinement statistics are shown in Table 2. The atomic coordinates and structure factors have been deposited in the Protein Data Bank, www.pdb.org (PDB ID: 4ROR).

(x) Clonal Phage Production

Forward and reverse sandwich oligos encoding the C-peptide clones were designed based on the primary sequence of each clone. The forward and reverse eboC37 oligos were: ATGCGGTACCTTTCTATTCTCATTCTTGGGGCG-GCACCTGCCATATTCTGGG CCCGGATTGCGCGATT-GAACCGCATGATTGGACCAAAA (SEQ ID NO: 9) and CCTTTTCGGCCGAACCCCCACCTTTATCCA-CAAAATCATGAATAATCTGATC AATTTTATCGG-TAATGTTTTTGGTCCAATCATGCGGTT (SEQ ID NO: 10). The forward and reverse eboC24 oligos were: ATGCG-GTACCTTTCTATTCTCATTCTATTGAACCGCATGAT-TGGACCAAAAA CATTACCG (SEQ ID NO: 11) and CCTTTTCGGCCGAACCCCCACCTTTATCCA-CAAAATCATGAATAATCTGATC AATTTTATCGG-TAATGTTTTTGGTCCAATCATGCGGTT (SEQ ID NO: 12). The oligo sandwich was annealed with 5 μg of each primer in 50 μL total volume in ddH₂O by heating to 95° C. and slow cooling and then extended with Klenow Fragment (New England Biolabs (NEB), Ipswich, Mass.) according to the manufacturer's protocol. The inserts and M13KE cloning vector backbone (NEB) were digested with Acc65I and Eagl-HF. The insert DNA was EtOH precipitated, gel purified from a 6% TBE acrylamide gel, extracted from the gel by incubating gel slices in a minimal volume of extraction buffer (100 mM NaOAc pH 4.5, 1 mM EDTA, 0.1% SDS) for 16 h at 37° C., and EtOH precipitated. The inserts and plasmid backbone were ligated and transformed into SS320 electrocompetent cells and plated on LB/IPTG/X-gal plates. The DNA from specific phage plaques was PCR amplified and Sanger sequenced (Eton Bioscience, Durham, N.C.), and those containing the correct DNA were subsequently amplified from a single plaque.

(xi) Phage Amplification

A single plaque was added to XL-1 Blue cells ($OD_{600}$ 0.5-1), diluted to 40 mL of $OD_{600}$ 0.05 in LB+25 μg/mL tetracycline, and shaken at 220 RPM at 37° C. for 4.5-5 hrs. Cells were pelleted by centrifugation, and the phage supernatant was sterile filtered. Phage were precipitated by adding $⅙^{th}$ volume of PEG-NaCl (20% w/v polyethylene glycol-8000 (Fisher Scientific, Pittsburgh, Pa.), 2.5 M NaCl) and incubating overnight at 4° C. Precipitated phage were then pelleted via centrifugation and resuspended in TBS (50 mM Tris-HCl, 150 mM NaCl, pH 7.4). They were PEG-precipitated again (~1 hr on ice), centrifuged and resuspended in 200 μL TBS. Aliquots were flash frozen and stored at −20° C. with a working stock left at 4° C. if imminent experiments were planned.

(xii) Clonal Phage Binding Assay

For each phage binding reaction, 30 μL streptavidin-coated magnetic beads (Life Technologies, Dynabeads MyOne, Streptavidin T1) at 10 mg/mL were magnetically pelleted and washed with 3.3× bead volume TBS. The beads were then blocked in 3.3× bead volume 100% SB (Thermo Scientific, SuperBlock Blocking Buffer in TBS, pH 7.4) for 10 min at RT and rinsed with equal volume of 100% SB* (SB adjusted to pH 5.8 with HCl). Solution-phase beads were then resuspended in 3.3× bead volume of 100% SB* and stored at 4° C. for up to 24 hrs. Solid-phase beads were resuspended in 3.3× bead volume PBS*+10% SB*. To load target onto solid-phase beads, 1× bead volume of an appropriate target concentration (e.g., 10 μL of 10 μM target for 10 μL beads) was added and incubated for 10 min followed by adding 3.3× bead volume 5 mM D-Biotin (in PBS*+10% SB*) and incubating for an additional 5 minutes. For blank (no target) beads, 3.3× bead volume of 5 mM D-Biotin was added and incubated for 5 minutes. All beads were then magnetically pelleted, washed in PBS* and resuspended in 1× bead volume PBS*+10% SB*.

Solid-phase binding reactions were incubated in 96-well format (Costar, sterile polystyrene, V-bottom, non-treated, Corning, Corning, N.Y.) with shaking at 700 rpm for 2 hrs at RT either as 30 or 100 μL reactions in 1×PBST* (PBS*+0.01% Tween-20)+10% SB* and $10^{10}$ plaque-forming units (pfu) of the phage clone. All washes and elution were done on the KingFisher Duo magnetic particle processor (Thermo Scientific). The binding reaction was mixed on the King-Fisher for 1 min at medium speed and the beads collected by 5 sec dips of the magnet through the sample, repeated 5 times (5×5 sec). All washes were done with PBST* (wash 1: 700 μL; wash 2: 800 μL; wash 3: 900 μL; washes 4-7: 1000 μL), mixed at slow speed for 1.5 min, and beads collected 3×3 sec. Bound phage were eluted with 50 μL EB (0.2 M glycine, pH 2.2) for 10 min, beads collected 5×5 sec, and neutralized with 7.5 μL NB (1 M Tris, pH 9.1). Dilutions of eluted phage were used to infect XL-1 Blue cells and then plated in top agar (40% LB agar/60% LB) on LB/IPTG/X-gal plates (LB agar, 25 µg/mL tetracycline, 1 mM IPTG, 0.1 mg/mL Xgal). Blue plaques were then counted to determine phage titers.

Solution-phase binding reactions were performed similarly to solid-phase 30 µL reactions. Instead of adding target-loaded beads to the binding reaction, an appropriate volume of 10× soluble target was added to the reaction (final 1× soluble target) just before phage were added. Additionally, on the Kingfisher Duo, target and bound phage were pulled down in a rapid 1 min magnetic pelleting step (1 min slow mixing, 5×5 sec bead collect). All washes were done with PBST* except wash 1 which contained 5 mM D-Biotin to block unoccupied streptavidin sites (wash 1: 150 µL; wash 2: 700 µL; wash 3: 800 µL; wash 4: 900 µL; wash 5: 1000 µL), mixed at slow speed for 25 sec, and beads collected 3×3 sec.

(xiii) Pseudovirus Infectivity Assays

Single-cycle pseudovirions were produced with a pNL4-3 HIV-1 genome (with firefly luciferase inserted into the nef gene and frameshift mutations in both Env and Vpr) and expressing filovirus GP on their surface (or VSV for a specificity control). These pseudovirions were produced by co-transfecting 293T human embryonic kidney cells with the described HIV-1 genome (pNL4-3.Luc.R-E-) and a plasmid encoding the desired virus glycoprotein (SV-ZeboGPAmuc for *Zaire ebolavirus* GP lacking the mucin domain, SV-MarVGP for *Marburg* Musoke GP and pMDG VSV-G for VSV) in the presence of PEI transfection reagent. Pseudovirus-containing supernatant was collected and filtered 38-43 hours post-transfection. For *ebolavirus* and *marburgvirus*, pseudovirions were concentrated by centrifuging through a 20% sucrose/TNE (10 mM Tris pH 7.6, 100 mM NaCl, 1 mM EDTA) cushion (26,000 RPM, 2 hours), and then the pellet was resuspended in TNE, aliquoted and stored at −80° C.

To measure inhibition of infectivity, 90 uL of each inhibitor dilution and 8.9 ug/mL DEAE-dextran were added to HOS-CD4-fusion cells in a 96-well format. For each assay, a total of six inhibitor dilutions were tested, each in quadruplicate. The plates were transferred to BSL3, and 10 uL of pseudovirus diluted in media was added to each well 30-60 minutes after the inhibitor addition (final DEAE-dextran concentration of 8 μg/mL). Virus was diluted in order to yield a robust luciferase signal. 24 hours later all wells were inspected under a light microscope to check for gross morphological changes. Virus and inhibitor were removed via aspiration, and fresh media was replenished. 20-24 hours later, the cells were lysed, and the luciferase activity was measured (Bright-Glo luciferase assay system, Promega, Madison, Wis.). To determine $IC_{50}$ values, the data from each inhibitor concentration series was normalized to the non-inhibitor control signal and fit to a Langmuir equation: $y=1/(1+[\text{inhibitor}]/IC_{50})$ (Kaleidagraph, Synergy Software, Reading, Pa.). The curve fit was weighted by the normalized standard error of each concentration point (with a minimum error allowed of 1%). Provided $IC_{50}$s are averages of two to four replicate experiments.

(xiv) Filovirus Immunofluorescence Assays

Vero cells were seeded in 96 well black plates. Peptides and vehicle control were diluted to 1.1× final concentration in culture media (MEM, 5% FBS, gentamicin (10 μg/mL)) and incubated on the plate for 1 hr at 37° C. In the BSL4 10 μL of virus diluted in media and DEAE-dextran was added to each well (final 8 μg/mL DEAE-dextran). *Ebola virus* (Kikwit, a representative strain of the *Zaire ebolavirus* species) and *Marburg virus* (Ci67) were diluted in culture media to yield a robust signal in the assay (~20% infected cells). After 1 hr at 37° C., the virus and peptides were removed, the wells were washed with PBS and media with peptide was used to replenish the wells. At 24 hours post-infection, each well was visualized via light microscope to look for any gross morphological abnormalities. At 48 hours post-infection, the wells were washed with PBS and then the cells fixed with 10% formalin. After blocking, the fixed cells were incubated with GP-specific mAb (9G4 for *Marburg virus*, KZ52 for *Ebola virus*) followed by incubation with FITC-labeled secondary antibody (goat anti-mouse or anti-human, respectively). Nuclei were stained with Hoechst solution. Cells were imaged using an Operetta high content device (PerkinElmer, Waltham, Mass.) and images were analyzed using Harmony software to determine percent of infected cells in a given well. Data were plotted normalized to the vehicle control.

TABLE 2 eboIZN21 crystallographic data and refinement statistics

| Data | |
|---|---|
| Crystal | JLEBO2 |
| Space Group | P321 (38.51, 38.51, 72.59) |
| Resolution (Å) | 40.0-2.15 |
| Resolution (Å) (high-resolution shell) | (2.23-2.15) |
| # Reflections measured | 94206 |
| # Unique reflections | 3693 |
| Redundancy | 25.6 |
| Completeness (%) | 99.9 (99.7) |
| <I/σI> | 18 (1.9) |
| Mosaicity (°) | 0.68 |
| Rpim[a] | 0.010 (0.234) |
| Refinement | |
| Resolution (Å) | 40.0-2.15 |
| Resolution (Å) - (high-resolution shell) | (2.46-2.15) |
| # Reflections used for refinement | 3281 |
| # Reflections in Rfree set | 355 |
| Rcryst[b] | 0.272 (0.316) |
| Rfree[c] | 0.294 (0.432) |
| RMSD: bonds (Å)/angles (°) | 0.002/0.503 |
| <B> ($Å^2$): all atoms/# atoms | 47.7/402 |
| <B> ($Å^2$): water molecules/#water | 55.4/6 |
| φ/ψ most favored (%)/additionally allowed (%) | 98/2 |

Values in parenthesis refer to data in the high resolution shell.

[a]Rpim = SQRT(1/N − 1) * Σ|I − <I>|/ΣI where I is the intensity of an individual measurement and <I> is the corresponding mean value − precision-indicating merging R-value.

[b]Rcryst = Σ||Fo| − |Fc||/Σ|Fo|, where |Fo| is the observed and |Fc| the calculated structure factor amplitude.

[c]Rfree is the same as Rcryst calculated with a randomly selected test set of reflections that were never used in refinement calculations.

REFERENCES

1. Sanchez A, Kahn A S, Zaki S R, Nabel G J, Ksiazek T G, Peters C J. 2001. Fields Virology, Lippincott, Williams, & Wilkins, Philadelphia.
2. Chronology of *Ebola* hemorrhagic fever outbreaks. http://www.cdc.gov/vhf/*ebola*/resources/outbreak-table.html Centers for Disease Control and Prevention; 2014.
3. Baize S, Pannetier D, Oestereich L, Rieger T, Koivogui L, Magassouba N, Soropogui B, Sow M S, Keita S, De Clerck H, Tiffany A, Dominguez G, Loua M, Traore A, Kolie M, Malano E R, Heleze E, Bocquin A, Mely S, Raoul H, Caro V, Cadar D, Gabriel M, Pahlmann M, Tappe D, Schmidt-Chanasit J, Impouma B, Diallo A K, Formenty P, Van Herp M, Gunther S (2014) Emergence of *Zaire Ebola Virus* Disease in Guinea-Preliminary Report. The New England journal of medicine. PMID: 24738640 {Medline}

4. Bossi P, Garin D, Guihot A, Gay F, Crance J M, Debord T, Autran B, Bricaire F (2006) Bioterrorism: management of major biological agents. Cell Mol Life Sci 63:2196-2212. PMID: 16964582 {Medline}
5. Volchkov V E, Feldmann H, Volchkova V A, Klenk H D (1998) Processing of the *Ebola virus* glycoprotein by the proprotein convertase furin. Proceedings of the National Academy of Sciences of the United States of America 95:5762-5767. PMID: 9576958 {Medline}
6. Volchkov V E, Volchkova V A, Stroher U, Becker S, Dolnik O, Cieplik M, Garten W, Klenk H D, Feldmann H (2000) Proteolytic processing of *Marburg virus* glycoprotein. Virology 268:1-6. PMID: 10683320 {Medline}
7. Chandran K, Sullivan N J, Felbor U, Whelan S P, Cunningham J M (2005) Endosomal proteolysis of the *Ebola virus* glycoprotein is necessary for infection. Science 308:1643-1645. PMID: 15831716 {Medline}
8. Schornberg K, Matsuyama S, Kabsch K, Delos S, Bouton A, White J (2006) Role of endosomal cathepsins in entry mediated by the *Ebola virus* glycoprotein. Journal of virology 80:4174-4178. PMID: 16571833 {Medline}
9. Carette J E, Raaben M, Wong A C, Herbert A S, Obernosterer G, Mulherkar N, Kuehne A I, Kranzusch P J, Griffin A M, Ruthel G, Dal Cin P, Dye J M, Whelan S P, Chandran K, Brummelkamp T R (2011) *Ebola virus* entry requires the cholesterol transporter Niemann-Pick C1. Nature 477:340-343. PMID: 21866103 {Medline}
10. Cote M, Misasi J, Ren T, Bruchez A, Lee K, Filone C M, Hensley L, Li Q, Ory D, Chandran K, Cunningham J (2011) Small molecule inhibitors reveal Niemann-Pick C1 is essential for *Ebola virus* infection. Nature 477:344-348. PMID: 21866101 {Medline}
11. Misasi J, Chandran K, Yang J Y, Considine B, Filone C M, Cote M, Sullivan N, Fabozzi G, Hensley L, Cunningham J (2012) Filoviruses require endosomal cysteine proteases for entry but exhibit distinct protease preferences. Journal of virology 86:3284-3292. PMID: 22238307 {Medline}
12. Eckert D M, Kim P S (2001) Mechanisms of viral membrane fusion and its inhibition. Annu Rev Biochem 70:777-810. PMID: 11395423 {Medline}
13. Lee J E, Saphire E O (2009) *Ebolavirus* glycoprotein structure and mechanism of entry. Future Virol 4:621-635. PMID: 20198110 {Medline}
14. White J M, Schornberg K L (2012) A new player in the puzzle of filovirus entry. Nat Rev Microbiol 10:317-322. PMID: 22491356 {Medline}
15. Harrison J S, Higgins C D, Chandran K, Lai J R (2011) Designed protein mimics of the *Ebola virus* glycoprotein GP2 alpha-helical bundle: stability and pH effects. Protein Sci 20:1587-1596. PMID: 21739501 {Medline}
16. Root M J, Steger H K (2004) HIV-1 gp41 as a target for viral entry inhibition. Curr Pharm Des 10:1805-1825. PMID: 15180542 {Medline}
17. Francis J N, Redman J S, Eckert D M, Kay M S (2012) Design of a Modular Tetrameric Scaffold for the Synthesis of Membrane-Localized D-Peptide Inhibitors of HIV-1 Entry. Bioconjug Chem 23:1252-1258. PMID: 22545664 {Medline}
18. Geisbert T W, Lee A C, Robbins M, Geisbert J B, Honko A N, Sood V, Johnson J C, de Jong S, Tavakoli I, Judge A, Hensley L E, Maclachlan I (2010) Postexposure protection of non-human primates against a lethal *Ebola virus* challenge with RNA interference: a proof-of-concept study. Lancet 375:1896-1905. PMID: 20511019 {Medline}
19. Warren T K, Warfield K L, Wells J, Swenson D L, Donner K S, Van Tongeren S A, Garza N L, Dong L, Mourich D V, Crumley S, Nichols D K, Iversen P L, Bavari S (2010) Advanced antisense therapies for postexposure protection against lethal filovirus infections. Nat Med 16:991-994. PMID: 20729866 {Medline}
20. Marzi A, Feldmann H, Geisbert T W, Falzarano D (2011) Vesicular Stomatitis Virus-Based Vaccines for Prophylaxis and Treatment of Filovirus Infections. J Bioterr Biodef 51. PMID: 22288023 {Medline}
21. Dye J M, Herbert A S, Kuehne A I, Barth J F, Muhammad M A, Zak S E, Ortiz R A, Prugar L I, Pratt W D (2012) Postexposure antibody prophylaxis protects nonhuman primates from filovirus disease. Proceedings of the National Academy of Sciences of the United States of America 109:5034-5039. PMID: 22411795 {Medline}
22. Qiu X, Audet J, Wong G, Pillet S, Bello A, Cabral T, Strong J E, Plummer F, Corbett C R, Alimonti J B, Kobinger G P (2012) Successful treatment of *ebola virus*-infected cynomolgus macaques with monoclonal antibodies. Sci Transl Med 4:138ra181. PMID: 22700957 {Medline}
23. Eckert D M, Malashkevich V N, Hong L H, Carr P A, Kim P S (1999) Inhibiting HIV-1 entry: discovery of D-peptide inhibitors that target the gp41 coiled-coil pocket. Cell 99:103-115. PMID: 10520998 {Medline}
24. Eckert D M, Kim P S (2001) Design of potent inhibitors of HIV-1 entry from the gp41 N-peptide region. Proc Natl Acad Sci USA 98:11187-11192. PMID: 11572974 {Medline}
25. Eckert D M, Malashkevich V N, Kim P S (1998) Crystal structure of GCN4-pIQI, a trimeric coiled coil with buried polar residues. J Mol Biol 284:859-865. PMID: 9837709 {Medline}
26. Weissenhorn W, Carfi A, Lee K H, Skehel J J, Wiley D C (1998) Crystal structure of the *Ebola virus* membrane fusion subunit, GP2, from the envelope glycoprotein ectodomain. Mol Cell 2:605-616. PMID: 9844633 {Medline}
27. Malashkevich V N, Schneider B J, McNally M L, Milhollen M A, Pang J X, Kim P S (1999) Core structure of the envelope glycoprotein GP2 from *Ebola virus* at 1.9-A resolution. Proc Natl Acad Sci USA 96:2662-2667. PMID: 10077567 {Medline}
28. Welch B D, VanDemark A P, Heroux A, Hill C P, Kay M S (2007) Potent D-Peptide Inhibitors of HIV-1 Entry. Proc Natl Acad Sci USA 104:16828-16833. PMID: 8846219 {Medline}
29. Chan D C, Fass D, Berger J M, Kim P S (1997) Core structure of gp41 from the HIV envelope glycoprotein. Cell 89:263-273. PMID: 9108481 {Medline}
30. Weissenhorn W, Dessen A, Harrison S C, Skehel J J, Wiley D C (1997) Atomic structure of the ectodomain from HIV-1 gp41. Nature 387:426-430. PMID: 9163431 {Medline}
31. Welch B D, Francis J N, Redman J S, Paul S, Weinstock M T, Reeves J D, Lie Y S, Whitby F G, Eckert D M, Hill C P, Root M J, Kay M S (2010) Design of a potent D-peptide HIV-1 entry inhibitor with a strong barrier to resistance. Journal of virology 84:11235-11244. PMID: 20719956 {Medline}
32. Salerno W J, Seaver S M, Armstrong B R, Radhakrishnan I (2004) MONSTER: inferring non-covalent interactions in macromolecular structures from atomic coordinate data. Nucleic Acids Res 32:W566-568. PMID: 15215451 {Medline}

33. Miller M D, Geleziunas R, Bianchi E, Lennard S, Hrin R, Zhang H, Lu M, An Z, Ingallinella P, Finotto M, Mattu M, Finnefrock A C, Bramhill D, Cook J, Eckert D M, Hampton R, Patel M, Jarantow S, Joyce J, Ciliberto G, Cortese R, Lu P, Strohl W, Schleif W, McElhaugh M, Lane S, Lloyd C, Lowe D, Osbourn J, Vaughan T, Emini E, Barbato G, Kim P S, Hazuda D J, Shiver J W, Pessi A (2005) A human monoclonal antibody neutralizes diverse HIV-1 isolates by binding a critical gp41 epitope. Proc Natl Acad Sci USA 102:14759-14764. PMID: 16203977 {Medline}

34. Montgomery D L, Wang Y J, Hrin R, Luftig M, Su B, Miller M D, Wang F, Haytko P, Huang L, Vitelli S, Condra J, Liu X, Hampton R, Carfi A, Pessi A, Bianchi E, Joyce J, Lloyd C, Geleziunas R, Bramhill D, King V M, Finnefrock A C, Strohl W, An Z (2009) Affinity maturation and characterization of a human monoclonal antibody against HIV-1 gp41. MAbs 1:462-474. PMID: 20065653 {Medline}

35. Schumacher T N, Mayr L M, Minor D L, Jr., Milhollen M A, Burgess M W, Kim P S (1996) Identification of D-peptide ligands through mirror-image phage display. Science 271:1854-1857. PMID: 8596952 {Medline}

36. Weinstock M T, Francis J N, Redman J S, Kay M S (2012) Protease-resistant peptide design-empowering nature's fragile warriors against HIV. Biopolymers 98:431-442. PMID: 23203688 {Medline}

37. Zawadzke L E, Berg J M (1992) A racemic protein. Journal of the American Chemical Society 114:4002-4003.

38. Dintzis H M, Symer D E, Dintzis R Z, Zawadzke L E, Berg J M (1993) A comparison of the immunogenicity of a pair of enantiomeric proteins. Proteins 16:306-308. PMID: 8346194 {Medline}

39. Noren K A, Noren C J (2001) Construction of high-complexity combinatorial phage display peptide libraries. Methods 23:169-178. PMID: 11181036 {Medline}

40. Hackenberger C P, Schwarzer D (2008) Chemoselective ligation and modification strategies for peptides and proteins. Angew Chem Int Ed Engl 47:10030-10074. PMID: 19072788 {Medline}

41. Blanco-Canosa J B, Dawson P E (2008) An efficient Fmoc-SPPS approach for the generation of thioester peptide precursors for use in native chemical ligation. Angew Chem Int Edit 47:6851-6855. PMID: ISI: 000258835300023 {Medline}

42. Wan Q, Danishefsky S J (2007) Free-radical-based, specific desulfurization of cysteine: a powerful advance in the synthesis of polypeptides and glycopolypeptides. Angew Chem Int Ed Engl 46:9248-9252. PMID: 18046687 {Medline}

43. Wild C, Greenwell T, Matthews T (1993) A synthetic peptide from HIV-1 gp41 is a potent inhibitor of virus-mediated cell-cell fusion. AIDS Res Hum Retroviruses 9:1051-1053. PMID: 8312047 {Medline}

44. Joshi S B, Dutch R E, Lamb R A (1998) A core trimer of the paramyxovirus fusion protein: parallels to influenza virus hemagglutinin and HIV-1 gp41. Virology 248:20-34. PMID: 9705252 {Medline}

45. Liu I J, Kao C L, Hsieh S C, Wey M T, Kan L S, Wang W K (2009) Identification of a minimal peptide derived from heptad repeat (HR) 2 of spike protein of SARS-CoV and combination of HR1-derived peptides as fusion inhibitors. Antiviral research 81:82-87. PMID: 18983873 {Medline}

46. Watanabe S, Takada A, Watanabe T, Ito H, Kida H, Kawaoka Y (2000) Functional importance of the coiled-coil of the Ebola virus glycoprotein. J Virol 74:10194-10201. PMID: 11024148 {Medline}

47. Miller E H, Harrison J S, Radoshitzky S R, Higgins C D, Chi X, Dong L, Kuhn J H, Bavari S, Lai J R, Chandran K (2011) Inhibition of Ebola virus entry by a C-peptide targeted to endosomes. J Biol Chem 286:15854-15861. PMID: 21454542 {Medline}

48. Higgins C D, Koellhoffer J F, Chandran K, Lai J R (2013) C-peptide inhibitors of Ebola virus glycoprotein-mediated cell entry: effects of conjugation to cholesterol and side chain-side chain crosslinking Bioorganic & medicinal chemistry letters 23:5356-5360. PMID: 23962564 {Medline}

49. Basu A, Li B, Mills D M, Panchal R G, Cardinale S C, Butler M M, Peet N P, Majgier-Baranowska H, Williams J D, Patel I, Moir D T, Bavari S, Ray R, Farzan M R, Rong L, Bowlin T L (2011) Identification of a small-molecule entry inhibitor for filoviruses. Journal of virology 85:3106-3119. PMID: 21270170 {Medline}

50. Roffey R, Tegnell A, Elgh F (2002) Biological warfare in a historical perspective. Clin Microbiol Infect 8:450-454. PMID: 12197867 {Medline}

51. Chen B K, Saksela K, Andino R, Baltimore D (1994) Distinct modes of human immunodeficiency virus type 1 proviral latency revealed by superinfection of nonproductively infected cell lines with recombinant luciferase-encoding viruses. J Virol 68:654-660. PMID: 7507183 {Medline}

52. Kuhn J H, Radoshitzky S R, Guth A C, Warfield K L, Li W, Vincent M J, Towner J S, Nichol S T, Bavari S, Choe H, Aman M J, Farzan M (2006) Conserved receptor-binding domains of Lake Victoria marburgvirus and Zaire ebolavirus bind a common receptor. J Biol Chem 281: 15951-15958. PMID: 16595665 {Medline}

53. Connor R I, Chen B K, Choe S, Landau N R (1995) Vpr is required for efficient replication of human immunodeficiency virus type-1 in mononuclear phagocytes. Virology 206:935-944. PMID: 7531918 {Medline}

54. He J, Choe S, Walker R, Di Marzio P, Morgan D O, Landau N R (1995) Human immunodeficiency virus type 1 viral protein R (Vpr) arrests cells in the G2 phase of the cell cycle by inhibiting p34cdc2 activity. J Virol 69:6705-6711. PMID: 7474080 {Medline}

55. Landau N R, Littman D R (1992) Packaging system for rapid production of murine leukemia virus vectors with variable tropism. J Virol 66:5110-5113. PMID: 1321291 {Medline}

56. Deng H, Liu R, Ellmeier W, Choe S, Unutmaz D, Burkhart M, Di Marzio P, Marmon S, Sutton R E, Hill C M, Davis C B, Peiper S C, Schall T J, Littman D R, Landau N R (1996) Identification of a major co-receptor for primary isolates of HIV-1. Nature 381:661-666. PMID: 8649511 {Medline}

57. Hamburger A E, Kim S, Welch B D, Kay M S (2005) Steric accessibility of the HIV-1 gp41 N-trimer region. J Biol Chem 280:12567-12572. PMID: 15657041 {Medline}

58. Sanchez A, Trappier S G, Mahy B W, Peters C J, Nichol S T (1996) The virion glycoproteins of Ebola viruses are encoded in two reading frames and are expressed through transcriptional editing. Proc Natl Acad Sci USA 93:3602-3607. PMID: 8622982 {Medline}

59. Studier F W (2005) Protein production by auto-induction in high density shaking cultures. Protein Expr Purif 41:207-234. PMID: 15915565 {Medline}

60. van den Berg S, Lofdahl P A, Hard T, Berglund H (2006) Improved solubility of TEV protease by directed evolution. J Biotechnol 121:291-298. PMID: 16150509 {Medline}
61. Blommel P G, Fox B G (2007) A combined approach to improving large-scale production of tobacco etch virus protease. Protein Expr Purif 55:53-68. PMID: 17543538 {Medline}
62. Blanco-Canosa J B, Dawson P E (2008) An efficient Fmoc-SPPS approach for the generation of thioester peptide precursors for use in native chemical ligation. Angew Chem Int Ed Engl 47:6851-6855. PMID: 18651678 {Medline}
63. Edelhoch H (1967) Spectroscopic determination of tryptophan and tyrosine in proteins. Biochemistry 6:1948-1954. PMID: 6049437 {Medline}
64. Cole J L (2004) Analysis of heterogeneous interactions. Methods Enzymol 384:212-232. PMID: 15081689 {Medline}
65. Laue T, Shah B, Ridgeway T, Pelletier S. Computer-aided interpretation of analytical sedimentation data for proteins. (1992) Analytical Ultrancentrifugation in Biochemistry and Polymer Science. Royal Society of Chemistry, Cambridge, UK.
66. Wohlfarth C. Partial specific volume of poly(ethylene glycol). In: Lechner M D, Arndt K F, Eds. (2010) Polymer Solutions. Springer-Verlag Berlin Heidelberg.
67. O'Shannessy D J, Brigham-Burke M, Soneson K K, Hensley P, Brooks I (1993) Determination of rate and equilibrium binding constants for macromolecular interactions using surface plasmon resonance: use of nonlinear least squares analysis methods. Anal Biochem 212:457-468. PMID: 8214588 {Medline}
68. Otwinowski Z, Minor W. Processing of X-ray diffraction data collected in oscillation mode. In: Carter J, C. W., Sweet R M, Eds. (1997) Methods in Enzymology. Academic Press, Inc., San Diego, pp. 307-326.
69. McCoy A J, Grosse-Kunstleve R W, Adams P D, Winn M D, Storoni L C, Read R J (2007) Phaser crystallographic software. J Appl Crystallogr 40:658-674. PMID: 19461840 {Medline}
70. Emsley P, Cowtan K (2004) Coot: model-building tools for molecular graphics. Acta Crystallogr D Biol Crystallogr 60:2126-2132.
71. Adams P D, Afonine P V, Bunkoczi G, Chen V B, Davis I W, Echols N, Headd J J, Hung L W, Kapral G J, Grosse-Kunstleve R W, McCoy A J, Moriarty N W, Oeffner R, Read R J, Richardson D C, Richardson J S, Terwilliger T C, Zwart P H (2010) PHENIX: a comprehensive Python-based system for macromolecular structure solution. Acta Crystallogr D Biol Crystallogr 66:213-221.
72. Chen V B, Arendall W B, 3rd, Headd J J, Keedy D A, Immormino R M, Kapral G J, Murray L W, Richardson J S, Richardson D C (2010) MolProbity: all-atom structure validation for macromolecular crystallography. Acta Crystallogr D Biol Crystallogr 66:12-21.
73. Jeffers S A, Sanders D A, Sanchez A (2002) Covalent modifications of the *ebola virus* glycoprotein. Journal of virology 76:12463-12472. PMID: 12438572 {Medline}
74. Henikoff S, Henikoff J G (1992) Amino acid substitution matrices from protein blocks. Proceedings of the National Academy of Sciences of the United States of America 89:10915-10919. PMID: 1438297 {Medline}

This application claims benefit under 35 U.S.C. § 119(e) to U.S. Provisional Application No. 62/054,835 filed on Sep. 24, 2014, which application is incorporated by reference herein in its entirety.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An *Ebolavirus* N-trimer mimic comprising a homotrimer of peptide monomers, wherein each peptide monomer comprises an an amino acid sequence of SEQ ID NO:23 or SEQ ID NO:21.

2. The *Ebolavirus* N-trimer mimic of claim 1, wherein each peptide monomer comprises an amino acid sequence of SEQ ID NO:23.

3. The *Ebolavirus* N-trimer mimic of claim 1, wherein each peptide monomer comprises an amino acid sequence of SEQ ID NO:21.

4. A pharmaceutical composition comprising an *Ebolavirus* N-trimer mimic of claim 1, and a pharmaceutically acceptable carrier.

5. A method of inhibiting *Ebolavirus* entry into a cell exposed to *Ebolavirus*, the methods comprising delivering an *Ebolavirus* N-trimer mimic of claim 1 to the cell exposed to *Ebolavirus*.

6. The method of claim 5, wherein the cell is human.

* * * * *

UNITED STATES PATENT AND TRADEMARK OFFICE
CERTIFICATE OF CORRECTION

PATENT NO. : 10,189,878 B2
APPLICATION NO. : 15/513959
DATED : January 29, 2019
INVENTOR(S) : Tracy R. Clinton Page 1 of 1

It is certified that error appears in the above-identified patent and that said Letters Patent is hereby corrected as shown below:

In the Specification

Column 1 Line 7, delete:
"This invention was made with government support under Grant No. AI102347 awarded by National Institutues of Helath, Grant No. GM82545 awarded by National Institutes of Health. The government has certain rights in this invention."

And replace it with the following:
--This invention was made with government support under grant AI076168 awarded by the National Institutes of Health. The government has certain rights in this invention.--

Signed and Sealed this
Seventeenth Day of September, 2019

Andrei Iancu
*Director of the United States Patent and Trademark Office*